United States Patent [19]

Cama et al.

[11] 4,058,661

[45] Nov. 15, 1977

[54] 7-DIACYL CEPHALOSPORINS

[75] Inventors: Lovji D. Cama, Edison; Burton G. Christensen, Metuchen; Sandor Karady, Mountainside; Meyer Sletzinger, North Plainfield, all of N.J.

[73] Assignee: Merck & Co., Inc., Rahway, N.J.

[21] Appl. No.: 565,495

[22] Filed: Apr. 7, 1975

Related U.S. Application Data

[60] Division of Ser. No. 356,873, May 3, 1973, abandoned, which is a continuation-in-part of Ser. No. 149,364, June 2, 1971, and Ser. No. 223,005, Feb. 2, 1972, abandoned, which is a continuation-in-part of Ser. No. 149,364, June 2, 1971.

[51] Int. Cl.$^2$ .................. C07D 501/46; C07D 501/44; C07D 501/42; C07D 501/40
[52] U.S. Cl. ..................... 544/21; 424/246; 544/22; 544/28; 544/30; 544/16; 544/26
[58] Field of Search ..................... 260/243 C

[56] References Cited

U.S. PATENT DOCUMENTS

| | | | |
|---|---|---|---|
| 3,897,424 | 7/1975 | Koppel et al. | 260/243 C |
| 3,910,902 | 10/1975 | Dolfini et al. | 260/243 C |
| 3,926,954 | 12/1975 | Kiesewetter et al. | 260/239.1 |

FOREIGN PATENT DOCUMENTS 2,225,437  11/1974  France

*Primary Examiner*—Nicholas S. Rizzo
*Assistant Examiner*—Diana G. Rivers
*Attorney, Agent, or Firm*—Hesna J. Pfeiffer; Julian S. Levitt

[57] ABSTRACT

New 7-diacylimido cephalosporins are produced by reacting 7-acylamido cephalosporins with an acylating agent in the presence of a silyl reagent. The 7-diacylimido cephalosporins are cleaved to produce cephalosporins containing a different acylamido moiety. Thus, the aminoadipoyl group of cephalosporins produced by fermentation is replaced by a different acyl group by the process of the present invention. The cephalosporins produced are antibiotics having enhanced activity against gram-negative and gram-positive pathogens.

5 Claims, No Drawings

7-DIACYL CEPHALOSPORINS

CROSS-REFERENCE TO RELATED APPLICATIONS

This is a division of application Ser. No. 356,873, filed May 3, 1973, now abandoned, which in turn is a continuation-in-part of copending application, U.S. Ser. No. 149,364, filed June 2, 1971 and of copending application, U.S. Ser. No. 223,005, filed Feb. 2, 1972, now abandoned; which in turn was a continuation-in-part of copending application, U.S. Ser. No. 149,364, filed June 2, 1971.

BACKGROUND OF THE INVENTION

One method of producing cephalosporins used medicinally as antibiotics comprises converting cephalosporin C to 7-aminocephalosporanic acid and then acylating this product to produce the desired 7-acylamidocephalosporin. This method suffers from the disadvantage that it is necessary to first isolate and purify the intermediate 7-aminocephalosporanic acid. Accordingly, other methods have been sought which would avoid the need of preparing the 7-aminocephalosporanic acid.

More recently it has also been found that cephalosporins having a methoxy substituent in place of the hydrogen substituent at C-7 are produced by various microorganisms. These cephalosporins likewise contain an aminoadipoyl group, and it is desired to replace this aminoadipoyl group with other acyl groups in order to provide new cephalosporins of enhanced antibiotic activity.

SUMMARY OF THE INVENTION

In accordance with the present invention, we have found that cephalosporin compounds can be transacylated as follows:

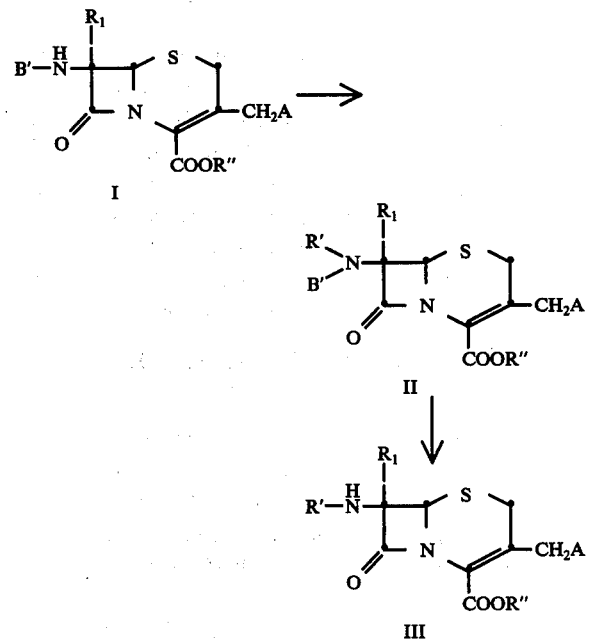

in which B' and R' represent acyl groups, $R_1$ represents hydrogen or a substituent such as methoxy, R" represents hydrogen or a blocking group and A represents hydrogen or an organo substituent unaffected during the described reactions or reconvertible thereto by the removal of any blocking or protecting groups.

Thus, in the above flowsheet the cephalosporin compound I is reacted with an acylating agent in the presence of a silyl reagent to produce the 7-diacylamido cephalosporin compound (II) which is then cleaved to produce the new 7-acylamido cephalosporin compound (III).

The step of producing the diacylated product is best effected by intimately contacting the cephalosporin compound with an acylating agent in a suitable solvent medium in the presence of the silyl reagent. The temperature at which the reaction is carried out is not particularly critical and temperatures from about $-20°$ C. to about $100°$ C. are generally satisfactory, although we prefer to carry out the reaction at temperatures from about $25°$ C. to $70°$ C. Solvents which do not contain an active hydrogen such as chloroform, acetonitrile, methylene chloride, dioxane, benzene, halobenzene, carbon tetrachloride, diethylether, and the like are suitable mediums for carrying out this reaction.

The acylating agent can be an acyl halide, an anhydride, or a mixed anhydride although generally it is preferred to use an acyl halide, for example an acyl chloride, as the acylating agent.

Silicon-nitrogen compounds are useful as silyl reagents in carrying out the processes of the present invention. Thus, silicon-nitrogen compounds of the general formula

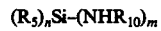

wherein $R_5$ represents alkyl, aryl or aralkyl groups having 1–8 carbon atoms or substituted alkyl, aryl or aralkyl groups having a cyano substituent or halo substituents, $n$ represents 2 or 3, $R_{10}$ represents a group containing an acyl group of a carbonic acid, a carboxylic acid, carbamic acid, sulfonic acid, sulfamic acid, sulfinic acid, a phosphonic acid, phosphoric acid, and the like. Examples of these silyl reagents that might be mentioned are those of the formulas

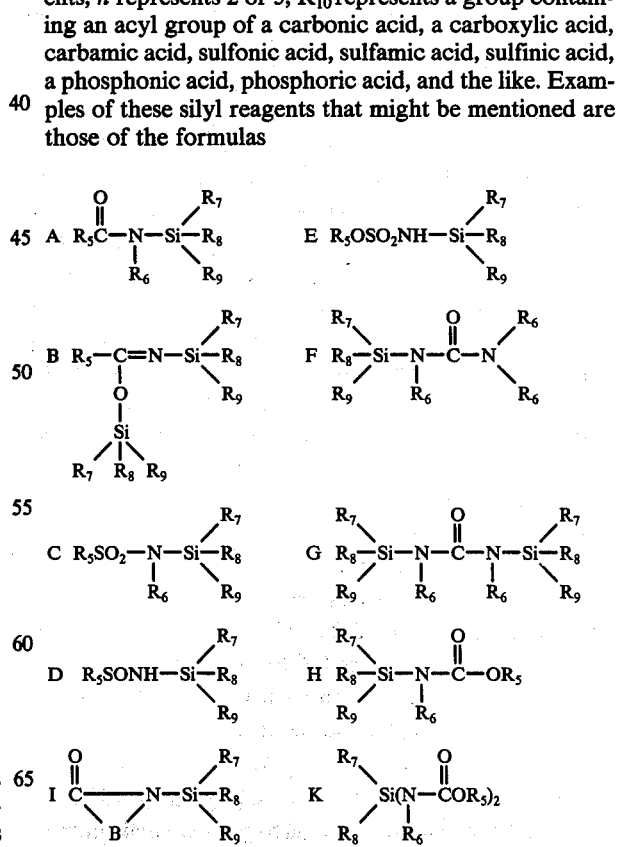

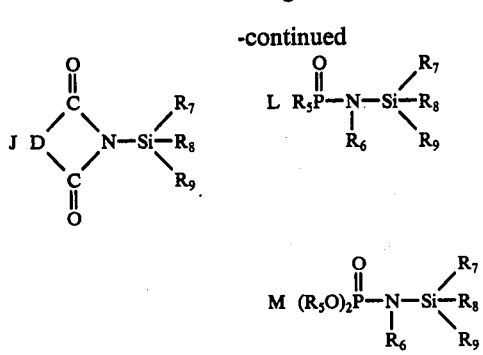

In the above formulas, $R_5$ is as defined above; $R_6$ represents hydrogen or $R_5$; $R_7$, $R_8$ and $R_9$ represent alkyl, aryl or aralkyl substituents containing 1–8 carbon atoms; B represents an alkylene group having 2–5 carbon atoms; and D represents B or a monocyclic aryl group. Specific silylating agents that might be mentioned are trihydrocarbylsilyl amides such as N-(trimethylsilyl)acetamide, N-(tripropylsilyl)acetamide, N-(tributylsilyl)acetamide, N-(triphenylsilyl)acetamide or N-(tribenzylsilyl)acetamide, N,O-bis(trimethylsilyl)acetamide, N,O-bis(triphenylsilyl)-acetamide, N,O-bis(tribenzylsilyl)acetamide, N-(trimethyl-silyl)trifluoroacetamide, N-(tributylsilyl)trifluoroacetamide, N-(trimethylsilyl)benzoamide, a silyl substituted urea such as N-(trimethylsilyl)diphenylurea, a N,N-bis(-trimethylsilyl)-diphenylurea, a silyl urethane such as N-(trimethylsilyl)-ethylcarbamate, a silyl imide such as N-triphenylsuccinimide or N-(trimethylsilyl)phthalimide, a silyl sulfonamide such as N-(trimethylsilyl)benzene sulfonamide, a dialkyl, diaryl or a diaralkyl silyl reagent such as bis(ethoxycarbonylamino)dimethyl silane and the like.

The substituent at the 3-position in I, II and III above, namely, —CH$_2$A, represents hydrogen or various substituents which are well known in the cephalosporin art. Thus, when A is hydroxy it includes the lactone formed with the carboxy group at 4, and when A is amino it includes the lactam formed with the carboxy group at 4. The substituent A also represents azido, halo, cyano, alkoxy, aryloxy, aralkyloxy, heterocycleoxy, mercapto, alkylthio, arylthio, aralkylthio, heterocyclethio, amino, alkylamino, alkanoylamino, hydroxyphenyl, acylthio, acyloxy, sulfamoyloxy, and the like. The heterocycles can be a 5- or 6-membered hetero ring containing one or more nitrogen, oxygen or sulfur atoms. The acyl group can be a loweralkanoyl group of 2–6 carbon atoms, carbamoyl, or thiocarbamoyl and N-alkyl or N,N-dialkyl derivatives thereof. The alkyl group of the foregoing substituents contains 1–6 carbon atoms and may be further substituted radicals such as alkoxy, halo, amino, cyano, carboxy, sulfo and the like.

The acyl substituents represented by B and R' in formulas I, II and III above are preferably carboxylic acid radicals. Examples of such radicals that might be mentioned are those of the general formula $R_{11}R_{10}CHCO$ wherein $R_{10}$ and $R_{11}$ are as defined below represent a preferred group of substituents because of their generally useful antibiotic activity. $R_{10}$ represents hydrogen, halo, amino, guanidino, phosphono, hydroxy, tetrazolyl, carboxy, sulfo or sulfamino. $R_{11}$ represents phenyl, substituted phenyl, a monocyclic heterocyclic 5- or 6-membered ring containing one or more oxygen, sulfur or nitrogen atoms in the ring, substituted heterocycles, phenylthio, heterocyclic or substituted heterocyclic thio groups; or cyano. The substituents can be halo, carboxymethyl, guanidino, guanidinomethyl, carboxaminomethyl, aminomethyl, nitro, methoxy or methyl. Examples of these preferred substituents that might be mentioned are phenacetyl, 3-bromophenylacetyl, p-aminomethylphenyl-acetyl, 4-carboxylmethylphenylacetyl, 4-carboxamidomethyl-phenylacetyl, 2-furylacetyl, 5-nitrofurylacetyl, 3-furylacetyl, 2-thienylacetyl, 5-chlorothienylacetyl, 5-methoxythienylacetyl, α-guanidino-2-thienylacetyl, 3-thienylacetyl, 4-methylthienylacetyl, 3-isothiazolylacetyl, 4-methoxyisothiazolylacetyl, 4-isothiazolylacetyl, 3-methylisothiazolylacetyl, 5-isothiazolylacetyl, 3-chloroisothiazolylacetyl, 3-methyl-1,2,5-oxadiazolylacetyl, 1,2,5-thiadiazolyl-4-acetyl, 3-methyl-1,2,5-thiadiazolyl-4-acetyl, 3-chloro-1,2,5-thiadiazolyl-4-acetyl, 3-methoxy-1,2,5-thiadiazolyl-4-acetyl, phenylthioacetyl, 4-pyridylthioacetyl, cyanoacetyl, tetrazolylacetyl, α-fluorophenylacetyl, D-phenylglycyl, 3-hydroxy-D-phenylglycyl, 2-thienylglycyl, 3-thienylglycyl, phenylmalonyl, 3-chlorophenylmalonyl, 2-thienylmalonyl, 3-thienylmalonyl, α-phosphonophenylacetyl, α-sulfaminophenylacetyl, α-hydroxyphenylacetyl, α-tetrazolylphenylacetyl and α-sulfophenylacetyl.

The step of cleaving the original acyl group can be effected in several ways, namely, by prolonging the reaction time, by the addition of an alcohol such as a loweralkanol or loweralkyl thiol, or by hydrolysis in an aqueous solution containing a small amount of an acid or a base. Thus, in some cases cleavage is effected by the addition of a loweralkanol or loweralkyl thiol containing from 1–6 carbon atoms, an aralkanol such as benzyl alcohol or a corresponding thiol and with other compounds the cleavage is effected by aqueous hydrolysis.

DESCRIPTION OF THE PREFERRED EMBODIMENTS

In accordance with a preferred embodiment of the present invention, it is now found that cephalosporins obtained by fermentation can be converted to derivatives having a different acyl group in place of the aminoadipoyl group without first cleaving this group and then reacylating the intermediate 7-amino compound. The process of this invention, therefore, provides a facile means of producing cephalosporin compounds and valuable intermediate products useful in this process. The general process is illustrated in the following flowsheet:

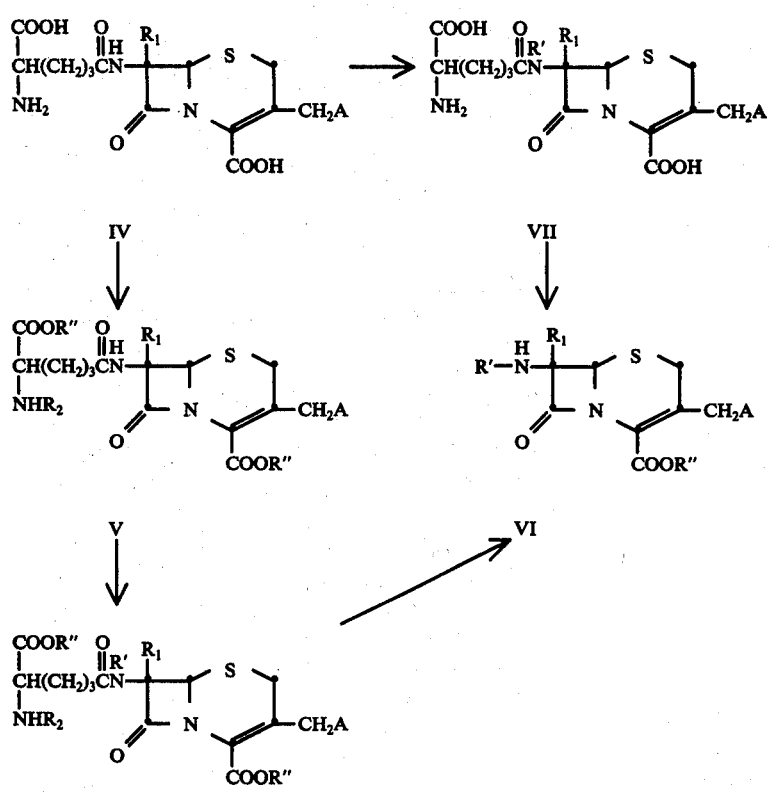

In the formulas of the above flowsheet, $R_1$ represents hydrogen or methoxy, A represents hydrogen or a substituent unaffected during the described reactions or reconvertible thereto by the removal of any protecting or blocking groups, R' represents an acyl group, R" represents hydrogen or a blocking or protecting substituent and $R_2$ represents a blocking or protecting substituent.

In accordance with the above flowsheet, the cephalosporin compound IV or a derivative thereof wherein the amino substituent and/or the carboxy groups are blocked or protected (V) is reacted with an acylating agent in the presence of a silyl compound to produce the intermediate diacylated product (VI or VII). The aminoadipoyl moiety of the latter product is then selectively cleaved to produce the new acylated cephalosporin compound (VIII), or a salt thereof when R" is hydrogen.

Although the process of our invention can be carried out without blocking or protecting the amino and carboxy groups of the starting cephalosporin compound, we generally prefer to carry it out by first blocking or protecting both the amino and carboxy groups since maximum yields of the desired new cephalosporin compound are obtained with such protected compounds.

An illustrative, more detailed description of this preferred process of our invention is shown in the following flowsheet:

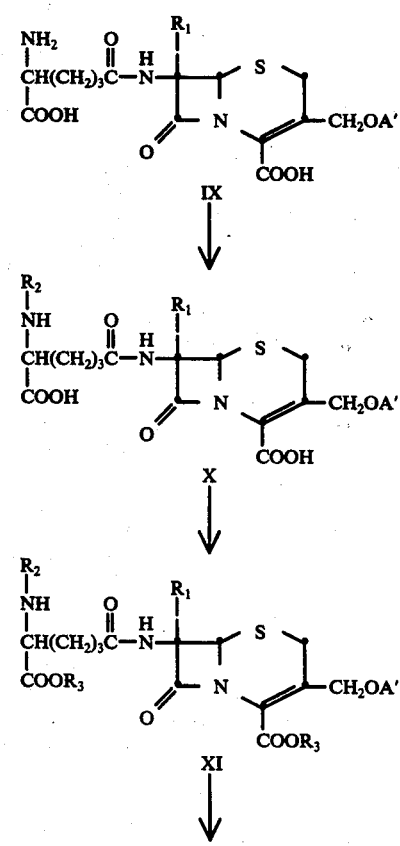

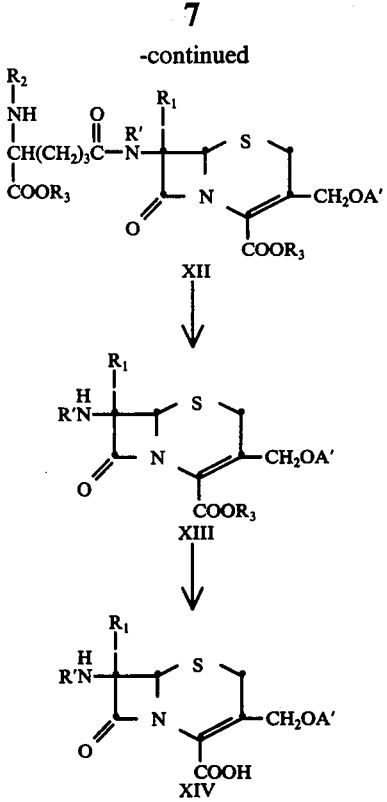

wherein $R_1$ represents hydrogen or methoxy, $R_2$ and $R_3$ represent blocking or protecting groups, $A'$ represents an acyl group and $R'$ represents an acyl group.

In accordance with this process, the amino group of the starting cephalosporin compound (IX) is first blocked by reaction with a suitable reagent to protect the 5'-amino-substituent. Thus, the amino group is blocked by amino protecting groups such as acyl, aroyl, alkoxycarbonyl, alkylsulfonyl, arylsulfonyl, and the like in accordance with methods well known in this art. Specific groups suitable for blocking the amino group that might be mentioned are trichloroethoxycarbonyl, tertiary butoxycarbonyl, benzoylmethoxycarbonyl, trimethylsilyl, p-methoxybenzyloxy, 2-nitrophenylsulfenyl, 2,4-dinitrophenylsulfenyl, chloroacetamido, o-nitrophenylthio and the like, although we generally prefer to utilize the trichloroethoxycarbonyl derivative which is conveniently prepared by reacting the cephalosporin compound with trichloroethoxycarbonyl chloride in the presence of an acid scavenger such as a base of a basic salt, for example a dialkyl phosphate, and the like.

It is generally preferred to carry out the above-described reactions with a cephalosporin compound wherein the carboxy group is likewise blocked or protected (XI) since maximum yields of the desired product are obtained with such derivatives. The blocking or protecting group is preferably one which can be removed to obtain the free acid without disruption of the β-lactam group since the cephalosporin compounds are usually used in the form of salts such as alkali metal salts or an amine salt. Protecting groups suitable for this purpose are well known in this art. Examples of suitable derivatives that might be mentioned are esters of alcohols, phenols, mercaptans, and thiophenols of the general formula —$COXR_4$ wherein $R_4$ represents the radical of an alcohol or a thiol such as methyl, ethyl, tertiary butyl, a substituted alkyl such as phthalimidomethyl, succinimidomethyl, phenacyl, a substituted phenacyl for example p-bromophenacyl, a β-substituted ethyl group such as 2,2,2-trichloroethyl, 2-methylthioethyl, 2-(p-methylphenyl)ethyl, 2-(p-methylphenyl)sulfonylethyl, 2-methylaminoethyl, 2-chloro(or bromo)ethyl, benzyl, a substituted benzyl group such as p-nitrobenzyl, p-methoxybenzyl, 3,5-dinitrobenzyl, 2,4,6-trimethylbenzyl, 3,5-dichloro-4-hydroxybenzyl, and the like, a benzhydryl or substituted benzhydryl group such as p-methoxybenzhydryl, an acyloxy alkyl group such as acetoxymethyl, pivaloyloxymethyl, an alkoxy group such as methoxymethyl, or a monocyclic aryl group for example phenyl or substituted phenyl such as p-nitrophenyl or 3,5-dinitrophenyl. These protecting or blocking groups for the carboxy substituents are readily prepared in accordance with processes well known in this art.

The protected cephalosporin compound is then reacted with an acylating agent in the presence of the silyl compound such as those described above to obtain the imide or diacylated product (XII). The acylating agent can be an acid halide (chloride or bromide), or a functional equivalent thereof such as an acid anhydride, a mercaptide, a mixed acid anhydride with other carboxylic acids, an activated ester of the carboxylic acid such as the p-nitrophenyl ester, and the like.

The preferred acylating agents used in the process of the present invention are those of carboxylic acids. The preferred acyl groups representing $R'$ in the above flowsheet are those of the general formula

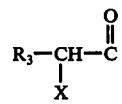

wherein X is hydrogen, halogen, amino, guanidino, phosphono, hydroxy, tetrazolyl, carboxy, sulfo, or sulfamino; $R_3$ is phenyl, substituted phenyl, a monocyclic heterocyclic 5- or 6-membered ring containing one or more oxygen, sulfur or nitrogen atoms in the ring, substituted heterocycles, phenylthio, phenyloxy, heterocyclic or substituted heterocyclic thio groups, loweralkyl (1–6 carbon atoms), or cyano; the substituents on the $R_3$ group being halo, carboxymethyl, guanidino, guanidinomethyl, carboxamidomethyl, aminomethyl, nitro, methoxy or methyl.

When the acylating agent contains groups such as amino or carboxy, these groups can be blocked or protected during the acylation reaction and later removed in accordance with methods known in this art. Alternatively, the acylating agent can contain a substituent such as azido which can be reduced to an amino substituent pursuant to known methods.

Especially preferred acylating agents that might be mentioned are those having an acetyl or substituted acetyl group such as phenylacetyl, thienylacetyl (2- and 3-thienylacetyl), furylacetyl (2- and 3-furylacetyl), phenoxyacetyl, phenylthioacetyl, α-azidophenylacetyl, and the like since the resulting acylated cephalosporin compounds have enhanced antibiotic activity.

The process of our invention is preferably carried out with a 3-$CH_2OA'$ cephalosporin compound wherein $A'$ represents an acyl group. Examples of such acyl groups that might be mentioned are loweralkanoyl ($C_2$–$C_6$), and especially acetyl, and carbamoyl since the cephalosporin compounds having such groups have enhanced antibiotic activity. Also, the acetyl group can be readily replaced to obtain other 3-substituted cephalosporins pursuant to methods well known in this art.

The silyl reagent is preferably a triorganosilyl or diorganosilyl compound such as those mentioned above. The trialkylsilyl compounds, and especially the trimethylsilyl compounds which are readily available, are particularly useful and preferred for this purpose. Examples of such compounds are the trialkylsilyl compounds shown in formulas A-M above, examples of which that might be mentioned are N-trimethylsilyl acetamide, N-trimethylsilyl trifluoroacetamide, N,O-bis(trimethylsilyl)acetamide, N,O-bis(trimethylsilyl)trifluoroacetamide, N-trimethylsilyl benzenesulfonamide, N-trimethylsilyl methylsulfonamide, N-trimethylsilyl urea, N,N-bis(trimethylsilyl)urea, N-trimethylsilyl-N,N'-diphenylurea, N-trimethylsilyl-N,N'-dimethylurea, N-trimethylsilyl ethylurethane, N-trimethylsilyl methylurethane, N-trimethylsilyl benzylurethane, N-trimethylsilyl succinimide, N-trimethylsilyl phthalimide, and other trialkylsilyl compounds such as the corresponding triethyl compounds.

The step of converting the protected cephalosporin compound (XI) to the imide to diacylated product (XII) is preferably effected by intimately contacting the cephalosporin compound with the acylating agent in a suitable solvent medium in the presence of the silyl compound. The temperature at which this reaction is carried out is not critical, and temperatures from about −20° C. to about 100° C. are generally satisfactory, although we prefer to carry out the reaction at temperatures from about 25° C. to 70° C. Various solvents which do not contain an active hydrogen such as chloroform, acetonitrile, methylene chloride, dioxane, benzene, halobenzene, carbon tetrachloride and diethylether are most suitable as mediums for the reaction mixtures.

The step of cleaving the original aminoadipoyl group can be effected in several ways, namely, by prolonging the reaction time, by the addition of an alcohol such as a loweralkanol or a loweralkyl thiol or by hydrolysis in an aqueous solution containing a small amount of an acid or a base. Thus, in some cases cleavage is effected by the addition of a loweralkanol or loweralkyl thiol containing from 1-6 carbon atoms, and aralkanol such as benzyl alcohol or the corresponding thiol. During the acylation reaction some cleavage of the aminoadipoyl group occurs, depending upon the conditions under which the acylation is effected. Thus, prolonged heating of the reaction mixture can result in the cleavage of the aminoadipoyl group and the preparation of the desired 7-acylated cephalosporin compound.

In accordance with a further embodiment of the present invention, it is found that the cleavage of the diacylated product or imide is also effected by reacting the imide with a silyl halide such as trimethylsilyl chloride. This process is readily carried out by heating the trimethylsilyl chloride with the imide in a suitable non-reactive solvent such as ethylene dichloride at about 60° C. for about 1 hour. The desired monoacylated cephalosporin compound is then recovered from the reaction mixture in accordance with procedures known in this art.

Alternatively, pursuant to another embodiment of this invention, it is found that during the acylation process spontaneous cleavage of the imide occurs depending upon the nature of the silyl reagent used. Thus, when an ester of 7β-(D-5-trichloroethoxycarbonylamino-5-carboxyvaleramido)-3-carbamoyloxymethyl-7-methoxy-3-cephem-4-carboxylic acid is reacted with 2-thienylacetyl chloride in the presence of N-trimethylsilyl benzene sulfonamide at 65° C. for about 10 hours, the corresponding ester of 3-carbamoyloxymethyl-7-methoxy-7β-(2-thienylacetamido)-3-cephem-4-carboxylic acid is isolated directly from the reaction mixture in good yield.

When the protecting group of the amino substituent of the aminoadipoyl moiety as a trichloroethoxycarbonyl or a t-butoxycarbonyl group is removed by suitable means, a selective cleavage of the aminoadipoyl group occurs. This removal of the protecting group of the amino function apparently results in an internal cyclization of the aminoadipoyl group resulting in cleavage of the group as the α-carboxylic ester of the formula

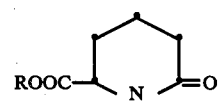

Our present evidence indicates that this is the mechanism of this cleavage; however, we do not wish to be bound by this explanation of how the cleavage occurs since subsequent studies may establish that the product is cleaved and extruded in some other manner. This explanation of how the cleavage occurs is presented to provide a better understanding of our invention.

The cleavage of the protective groups on the amino and carboxy functions is accomplished in accordance with procedures well known in this art. Thus, for example, the trichloroethoxycarbonyl group is removed by reaction with zinc and acetic acid, and the t-butoxycarbonyl and benzhydryl groups are removed by reaction with trifluoroacetic acid.

In accordance with a further aspect of our invention, new 7-diacylamido compounds obtained by our process are not only useful as intermediates in the preparation of the monoacylated cephalosporins but are useful antimicrobial products active against various pathogenic microorganisms.

EXAMPLE 1

3-Carbamoyloxymethyl-7-methoxy-7β-phenylacetamido-3-cephem-4-carboxylic Acid

Step A:
7β-(D-5-trichloroethoxycarbonylamino-5-carboxyvaleramido)-3-carbamoyloxymethyl-7-methoxy-3-cephem-4-carboxylic Acid The mono-sodium salt of 7β-(D-5-amino-5-carboxyvaleramido)-3-carbamoyloxymethyl-7-methoxy-3-cephem-4-carboxylic acid (20.5 gm.) is dissolved in the mixture of acetone (80 ml.) and aqueous 10% dipotassium hydrogen phosphate (240 ml.). To this solution is added dropwise trichloroethoxycarbonyl chloride (25 gm., 118 mmoles) in acetone (80 ml.). During the addition the pH of the solution is kept at 9.1 by gradual addition of 2.5 N sodium hydroxide solution. After 30 minutes the mixture is extracted with ethyl acetate, the ethyl acetate layer discarded, and the aqueous layer is acidified to pH 2.5 with concentrated hydrochloric acid. The precipitated product is extracted into ethyl acetate. After drying over sodium sulfate and removing the solvent in vacuo, the title compound is obtained as an oil.

UV: (CH$_3$OH) λmax. 262.5 ε=5450

NMR: (Solvent - DMSO, d$_6$) δ=3.43 (O-CH$_3$, s), 4.73 (2-H$_2$, partially visible, 4.81

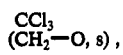

5.12 (6-H, s), ~4.74 (10-H$_2$, partially visible).

Step B: Di-benzhydryl ester of 7β-(D-5'-trichloroethoxycarbonylamino-5'-carboxyvaleramido)-3-carbamoyloxymethyl-7-methoxy-3-cephem-4-carboxylic Acid To the solution of the above 7β-(D-5-trichloroethoxycarbonylamino-5-carboxyvaleramido)-3-carbamoyloxymethyl-7-methoxy-3-cephem-4-carboxylic acid in ethyl acetate (500 ml.) is added diphenyldiazomethane (17 gm.) in 200 ml. of ether. After agitating the mixture overnight, it is extracted successively with sodium bicarbonate and sodium chloride solutions. The solvent is evaporated from the dried solution to afford a crude product which is purified by chromatography on silica gel. A 2:1 mixture of chloroform and ethyl acetate is used for elution. This material showed a single spot on TLC chromatography.

UV: (CH$_3$OH) λmax. 2650μm ε7000

NMR: (Solvent - CDCl$_3$) δ=3.45 (O-CH$_3$, s), 3.35 (2-H$_2$, partially visible, 4.69

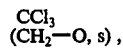

5.03 (6-H, s), ~4.88 (10-H$_2$, partially visible).

Step C: Di-benzhydryl ester of 7β-[(D-5'-trichloroethoxy-carbonylamino-5'-carboxyvaleryl)phenylacetylamino]-3-carbamoyloxymethyl-7-methoxy-3-cephem-4-carboxylic Acid A mixture of the di-benzhydryl ester of 7β-(D-5'-trichloroethoxycarbonylamino-5'-carboxyvaleramido)-3-carbamoyloxymethyl-7-methoxy-3-cephem-4-carboxylic acid (1.1 gm., 1.18 mmole), acetonitrile (5 ml.) and bis-trimethylsilyl trifluoroacetamide (3 ml.) is allowed to stand at room temperature for 6 hours. After this period, the volatile products are removed in high vacuum and the residue is dissolved in 3 ml. of methylene chloride. To this solution is added phenylacetyl chloride (0.23 ml., 1.79 mmole) and the mixture is allowed to stand at room temperature for 65 hours. After this, the solution is evaporated and the residue is dissolved in 5 ml. tetrahydrofuran and 0.7 ml. of 2.5 N hydrochloric acid. After 20 minutes reaction time the solvent is evaporated and the residue is partitioned between methylene chloride and soium bicarbonate solution. The organic layer is washed with sodium chloride solution, dried and evaporated to dryness. The crude product thus obtained is purified by chromatography on silica gel, using chloroform ethyl acetate 95:5 as eluant. The title compound obtained appears homogenous on thin layer chromatography.

UV: (CH$_3$OH) λmax. 2640μm ε6650

NMR: (Solvent - CDCl$_3$) δ=3.50 (O-CH$_3$, s), 3.31 (2-H$_2$, partially visible, 4.67

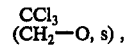

5.04 (6-H, s), ~4.96 (10-H$_2$, partially visible), 3.95 (13-H$_2$, s).

Step D: Benzhydryl ester of 3-carbamoyloxymethyl-7-methoxy-7β-phenylacetamido-3-cephem-4-carboxylic Acid The solution of di-benzhydryl ester of 7β-[(D-5'-trichloroethoxycarbonylamino-5'-carboxyvaleryl)-phenylacetylamino]-3-carbamoyloxymethyl-7-methoxy-3-cephem-4-carboxylic acid (104 mg.) in 90% acetic acid-water (1 ml.) is agitated with 100 mg. of zinc dust for 5 hours. After this, the solution is filtered and the solvent is removed in vacuo. The residue is partitioned between methylene chloride and water, and the methylene chloride layer is extracted with sodium bicarbonate and sodium chloride solutions. After drying and evaporation a crude product is obtained which is purified by thin layer chromatography utilizing silica gel plates and a 3:2 mixture of chloroform and ethyl acetate. The product is characterized by its IR and NMR spectra.

IR: (CHCl$_3$) 1780, 1730 and 1680 cm$^{-1}$

UV: (CH$_3$OH) λmax. 2640μm ε5870

NMR: (Solvent — CDCl$_3$) δ=3.40 (O-CH$_3$, s), 3.33 (2-H$_2$, partially visible), 5.01 (6-H, s), ~4.88 (10-H$_2$, partially visible), 3.60 (13-H$_2$, s).

Step E: 3-Carbamoyloxymethyl-7-methoxy-7β-phenylacetamido-3-cephem-4-carboxylic Acid Benzhydryl ester of 3-carbamoyloxymethyl-7-methoxy-7β-phenylacetamido-3-cephem-4-carboxylic acid (17 mg.) is dissolved in anisole (0.2 ml.) and treated with trifluoroacetic acid (0.5 ml.) for 5 minutes. After this period, the mixture is concentrated rapidly in high vacuum and diluted with ethyl acetate. The product is removed from the ethyl acetate solution by extraction with a pH 7.5 sodium phosphate buffer. The buffer solution is acidified to pH 2.5 with dilute hydrochloric acid and the title compound is removed by extraction with ethyl acetate. After drying and evaporating the solution, the product is obtained. An analytical sample is obtained by recrystallization from ethylacetate. MP: 159°–161° C.

UV: (pH 7 buffer) λmax. 2670μm ε8650. IR: (CH$_3$CN) 1780, 1735 and 1700. NMR: (solvent - CD$_3$CN + D$_2$O) δ = 3.42 (O-CH$_3$, s), 3.35 (2-H$_2$, partially visible), 5.01 (6-H, s), 4.83 (10-H$_2$, d), 3.61 (13-H$_2$, s).

Elemental analysis for C$_{18}$H$_{19}$O$_7$N$_3$S: Calc. - C, 51.29; H, 4.54; Found - C, 51.47; H, 4.73.

Two milligrams of the above acid is dissolved in 1 drop of methanol and treated with a solution of 2 mg. dibenzyl ethylenediamine diacetate in ethyl acetate. The dibenzyl ethylenediamine salt of the title compound precipitates after standing in the form of needle-like crystals. MP: 140°–143° C. UV: (CH$_3$OH) λmax. 263μm ε8600.

The starting material, the monosodium salt of 7β-(D-5-amino-5-carboxyvaleramido)-3-carbamoyloxymethyl-7-methoxy-3-cephem-4-carboxylic acid, used in the foregoing example is prepared as follows:

Preparation of Monosodium Salt of 7β-(D-5-amino-5-carboxyvaleramido)-3-carbamoyloxymethyl-7-methoxy-3-cephem-4-carboxylic Acid

Modified Fermentation Process:

Step 1: Slants

A lyophilized tube of *Streptomyces lactamdurans* culture (NRRL 3802) was opened asceptically and the organism transferred to a medium of the following composition:

Medium XI:
1% Blackstrap Molasses
1% National Brewer's Yeast
2.5% Difco agar pH 7.0
Water to volume The slants are inoculated for 7 days at 28° C. When stored in the cold, the slants are stable for more than 13 weeks.

Step 2: Seed Stages: Two Stage System

First Seed: The first seed is inoculated directly from the slant of Step 1 to 40 ml. of 1% Primary Dried Yeast N.F., pH 7.0 (obtained from the Yeast Product Corporation) in a 250 ml. baffled Erlenmeyer flask. The flasks were then shaken on a 220 rpm. rotary shaker with a 2 inch throw at 28° C. for a period of from 2 to 3 days.

Second Seed: A 2.5% inoculum from the first seed stage was added to a flask containing a 2% Fleischmann S-150 yeast autolysate, pH 7.0. The growth in this stage is characteristically light and the incubation, performed as in the first stage, was not extended beyond 48 hours.

Step 3: Production Medium

The production medium contains per liter of distilled water 30 g. distiller's solubles, 7.5 g. of primary dried yeast N.F. and 0.25% v/v of an emulsified petroleum product (Mobilpar-S)defoamer. The medium is adjusted to pH 7.0 with a small amount of concentrated sodium hydroxide solution dispensed into Erlenmeyer flasks and autoclaved for 15 or 20 minutes at 121° C. After cooling the medium received a 2.5% inoculum of the seed obtained in Step 2. The time of incubation can vary from about 50 to 100 hours but an incubation period of about 72 hours is preferred. The volume of media in each flask can vary from 30 to 50 ml. but 40 ml. was used routinely. The level of inoculum can vary from 1 to 5%, but, in practice, a 2.5% level is generally employed.

Step 4: Assay

When the fermentation was complete, the cells were removed by centrifugation and the broth was diluted with phosphate buffer, pH 7.0. The concentration of 7β-(D-5-amino-5-carboxyvaleramido)-3-carbamoyloxymethyl-7-methoxy-3-cephem-4-carboxylic acid in the fermentation broth was determined by the standard biological-disc assay method. The assay organism employed was *Vibrio percolans* (ATCC 8461). Filter paper discs are immersed into the diluted broths and placed on the surface of agar-containing Petri dishes which were inoculated with the assay organism *Vibrio percolans* (ATCC 8461). Also placed on these Petri dishes are discs that had been dipped previously in standard solutions containing known concentrations of 7β-(D-5-carboxyvaleramido)-3-carbamoyloxymethyl-7-methoxy-3-cephem-4-carboxylic acid. The discs were incubated overnight at 28° C. and the diameters of the zones of inhibition recorded. The concentration of product and the fermented broth is calculated by interpolation from the standard curve which relates zone diameter with the known concentrations of standard solutions of the product. By this procedure it was calculated that *Streptomyces lactamdurans* NRRL-3802 produced 78.6 μg/ml. of 7β-(D-5-amino-5-carboxyvaleramido)-3-carbamoyloxymethyl-7-methoxy-3-cephem-4-carboxylic acid in the modified fermentation process.

Step 5: Isolation

The filtered broth is adjusted to pH 7.0 with dilute hydrochloric acid and 2900 ml. is passed through a column containing a strongly basic anion exchange resin (100 g.) having a styrene-divinylbenzene matrix (Dowex 1 × 2 chloride cycle resin) at 10 ml./minute. The spent solvent is collected in 500 ml. fractions. The resin column is washed with water and eluted with 3% ammonium chloride in 90% methanol. The eluate is collected in 100 ml. fractions. The spent fractions are combined, the pH adjusted to pH 7.2 to 8.0 with dilute sodium hydroxide and adsorbed on a strongly basic anion exchange resin (100 g.) having a styrene-divinylbenzene matrix (Dowex 1 × 2 chloride cycle resin) at 14 ml/minute. The column is washed with water and eluted with 5% aqueous sodium chloride. The eluate is collected in 50 ml. fractions and concentrated. The concentrate is diluted to 500 ml., adjusted from pH 8.8 to pH 2.0 with dilute hydrochloric acid and adsorbed on 25 ml. of a strongly acidic cation exchange resin of the sulfonate type having a styrenedivinylbenzene matrix (Dowex 50 × 2 hydrogen cycle resin) at 2.5 ml./minute. The column is washed with 25 ml. of water then eluted with 2% pyridine until the pH of the column effluent rose to pH 7 (54 ml.). The eluate thus obtained is adjusted to pH 8.0 with dilute sodium hydroxide and concentrated under vacuum to remove the pyridine and afford the monosodium salt of 7β-(D-5-amino-5-carboxyvaleramido)-3-carbamoyloxymethyl-7-methoxy-3-cephem-4-carboxylic acid.

Elemental analysis for $C_{16}H_{21}N_4SO_9Na$:
Calc.: C, 41.0%; H, 4.5%; N, 12.0%; S, 6.8%; Found: C, 39.31%, H, 4.76%; N, 11.16%; S, 6.46%.

EXAMPLE 2

3-Carbamoyloxymethyl-7-methoxy-7β-phenylacetamido-3-cephem-4-carboxylic Acid

Step A: Di-benzhydryl ester of 7β-[(D-5'-trichloroethoxycarbonylamino-5'-carboxyvaleryl)phenylacetylamino]-3-carbamoyloxymethyl-7-methoxy-3-cephem-4-carboxylic Acid A solution of the di-benzhydryl ester of 7β-(D-5-trichloroethoxycarbonylamino-5-carboxyvaleramido)-3-carbamoyloxymethyl-7-methoxy-3-cephem-4-carboxylic acid (9.3 gm., 10 mmoles), N-trimethylsilyl phthalimide (7.8 gm., 40 mmoles) and phenylacetyl chloride (5.3 ml., 40 mmoles) in 50 ml. of acetonitrile is heated to 40° C. for 20 hours. After this period the mixture is cooled to room temperature and filtered. The filtrate is evaporated to dryness and triturated with hexane. The insoluble residue, containing di-benzhydryl ester of 7β-[(D-5'-trichloroethoxycarbonylamino-5'-carboxyvaleryl)phenylacetylamino]-3-carbamoyloxymethyl-7-methoxy-3-cephem-4-carboxylic acid, is used without purification in the next step.

Step B: Benzhydryl ester of 3-carbamoyloxymethyl-7-methoxy-7β-phenylacetamido-3-cephem-4-carboxylic Acid The crude product from Step A is dissolved in a mixture of ethylacetate (50 ml.), acetic acid (45 ml.) and water (5 ml.). To this solution is added 20 gm. of zinc powder and the mixture is agitated at room temperature for 4 hours. After this, the excess zinc is removed by filtration and the filtrate partitioned between ethylacetate and water. The organic layer is washed with a sodium bicarbonate solution and water, dried and the solvent is evaporated. The crude product thus obtained is purified by chromatography on 1 kg. of silica gel, using a mixture of chloroform, hexane, and methanol (47:47:6) for elution. The product obtained has the physical characteristics described in Example 1, Step E.

Step C: 3-Carbamoyloxymethyl-7-methoxy-7-phenylacetamido-3-cephem-4-carboxylic Acid The title compound is prepared by the procedure described in Example 1, Step F, and has the same physical characteristics as the product of Example 1.

EXAMPLE 3

3-Carbamoyloxymethyl-7-methoxy-7β-(2-thienylacetamido)-3-cephem-4-carboxylic Acid

Step A: Di-benzhydryl ester of 7β-[(D-5'-trichloroethoxy-carbonylamino-5'-carboxyvaleryl)-2-thienylacetyl-amino]-3-carbamoyloxymethyl-7-methoxy-3-cephem-4-carboxylic Acid A mixture of 6.0 gm. (6.3 mmole) of the dibenzhydryl ester of 7β-(D-5'-trichloroethoxycarbonylamino-5'-carboxyvaleramido)-3-carbamoyloxymethyl-7-methoxy-3-cephem-4-carboxylic acid, 4.7 gm. (40 mmoles) N-trimethylsilyl trifluoroacetamide, 3.42 ml. (25 mmoles) 2-thienylacetylchloride, and 50 ml. of chloroform is warmed at 47° C. for 16 hours. After the solvent is removed by evaporation, the crude reaction mixture is extracted with hexane, and further purified by chromatography on 1 kg. of silica gel using 10% ethylacetate in chloroform as the eluant.

UV: (CH$_3$OH) λmax. 265μm ε 5810
NMR: (Solvent - CDCl$_3$) δ=3.53 (—OCH$_3$, s), ~3.4 (2-H$_2$, d), 4.74

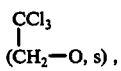

5.05 (6-H, s), ~5.0 (10-H$_2$, partially visible), 4.15 (13-H$_2$, s).

Step B: Benzhydryl ester of 3-carbamoyloxymethyl-7-methoxy-7β-(2-thienylacetamido)-3-cephem-4-carboxylic Acid The di-benzhydryl ester of 7β-[(D-50'-trichloroethoxycarbonylamino-5'-carboxyvaleryl)-3-thienylacetylamino]-3-carbamoyloxymethyl-7-methoxy-3-cephem-4-carboxylic acid (4.2 gm., 3.8 mmoles) is dissolved in 30 ml. of ethylacetate and added to 30 ml. of 90% aqueous acetic acid and 12 gm. of zinc dust. The mixture is stirred vigorously for 5 ½ hours at room temperature. After the zinc is filtered off, excess acetic acid is removed by washing the ethylacetate solution with water. The title compound is isolated in the same manner as described in Example 1, Step E. It is characterized by TLC (7% CH$_3$OH in 1:1 CHCl$_3$:n-hexane) as a single spot material.

IR: (CHCl$_3$) 1740, 1800 cm$^{-1}$;
UV: λmax. 263μm ε 5800
NMR: (Solvent - CDCl$_3$) δ=3.45 (—OCH$_3$, s), ~3.4 (2-H$_2$, d),
5.02(6-H, s), ~4.92 (10-H$_2$, partially visible), 3,85 (13-H$_2$, s).

Step C: 3-Carbamoyloxymethyl-7-methoxy-7β-(2-thienylacetamido)-3-cephem-4-carboxylic Acid A cold solution of the benzhydryl ester of 3-carbamoyloxymethyl-7-methoxy-7β-(2-thienylacetamido)-3-cephem-4-carboxylic acid (1.36 gm.) in 10.88 ml. of anisole is stirred with 5.44 ml. of trifluoroacetic acid at 0° C. for ½ hour. The volatiles are removed in high vacuum, and the product is recrystallized from ethyl acetate. MP: 165°–167° C.

UV: (pH 7 buffer) λmax. 263μm ε 8840 236μm ε 14000; [α]$_d$ (C=1, CH$_3$OH) = +199°
NMR: (Solvent - CD$_3$CN + D$_2$O) δ=3.48 (—OCH$_3$, s), ~3.4 (2-H$_2$, partially visible), 5.05 (6-H, s), 4.91 (10-H$_2$, d), 3.86 (13-H$_2$, s).

Elemental analysis for C$_{16}$H$_{17}$N$_3$O$_7$S$_2$:
Calc.: C, 44.96; H, 4.01; N, 9.83; Found: C, 44.86; H, 3.99; N, 9.21; S, 15.00.

EXAMPLE 4

3-Carbamoyloxymethyl-7β-(2-furylacetamido)-7-methoxy-3-cephem-4-carboxylic Acid

Step A- Di-benzhydryl ester of 7β-[(D-5'-trichloroethoxy-carbonylamino-5'-carboxyvaleryl)-2-furylacetyl-amino]-3-carbamoyloxymethyl-7-methoxy-3-cephem-4-carboxylic Acid A mixture of the di-benzhydryl ester of 7β-(D-5'-trichloroethoxycarbonylamino-5'-carboxyvaleramido)-3-carbamoyloxymethyl-7-methoxy-3-cephem-4-carboxylic acid (9.3 gm.), bis-(trimethyl-silyl)-trifluoroacetamide (7.0 ml.), 2-furylacetylchloride (4.7 ml.) and dichloromethane (50 ml.) is warmed at 47° C for 16 hours. The solvent is removed by evaporation, the crude reaction mixture is extracted with hexane, and the residue is used without purification in the next step.

NMR: (Solvent — CDCl$_3$) δ=3.48 (—OCH$_3$, s), 3.08 (2-H$_2$, d), 4.63

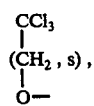

5.02 (6-H, s), ~4.88 (10-H$_2$, d), 3.72 (13-H$_2$, s).

Step B- Benzhydryl ester of 7β-(2-furyacetamido)-3-carbamoyloxymethyl-7-methoxy-3-cephem-4-carboxylic Acid The di-benzhydryl ester from Step A is reacted with zinc dust and acetic acid following the procedures described in Example 3 Step B. After crystallization from chloroformhexane, the pure product has the following physical characteristics:

MP: 168°–171° C.
IR: (CHCl$_3$) 1800, 1720, 1700
UV: λmax. 265μm ε 7200

NMR: (Solvent — CD$_3$CN) δ=3.43 (—OCH$_3$, s), 3.39 (2-H$_2$, partially visible), 5.0 (6-H, s), 4.75 (10-H$_2$, d), 3.64 (13-H$_2$, s).

Step C:
3-Carbamoyloxymethyl-7-methoxy-7β-(2-furylacetamido)-3-cephem-4-carboxylic Acid The 3-carbamoyloxymethyl-7-methoxy-7β-(2-furylacetamido)-3-cephem-4-carboxylic acid is prepared from the product of Step B following the procedure described in Example 3, Step C. The product, after recrystallization from ethyl acetate, has a melting point of 156°–161° C.

UV: (pH 7 buffer) λmax. 265βm ε 7200
IR is consistent with the structure.
NMR: (Solvent — CD$_3$CN + D$_2$O) δ=3.44 (—OCH$_3$, s), ~3.38 (2-H$_2$, partially visible), 5.02 (6-H, s), 4.82 (10-H$_2$, d), 3.66 (13-H$_2$, s).

EXAMPLE 5

3-Carbamoyloxymethyl-7-methoxy-7β-thiophenoxyacetamido-3-cephem-4-carboxylic Acid

Step A: Di-benzhydryl ester of 7β-[(D-5-Trichloroethoxycarbonylamino-5-carboxyvaleryl)thiophenoxyamido]-3-carbamoyloxymethyl-7-methoxy-3-cephem-4-carboxylic Acid By following substantially the procedure described in Example 4, Step A, and by substituting for the 2-furylacetyl chloride an equimolar quantity of phenylthioacetyl chloride there is obtained di-benzhydryl ester of 7β-[(D-5-trichloroethoxycarbonylamino-5-carboxyvaleryl)thiophenoxyamido]-3-carbamoyloxymethyl-7-methoxy-3-cephem-4-carboxylic acid.

NMR: (Solvent — CDCl$_3$) δ=3.33 (—OCH$_3$, s), ~3.23 (2-H$_2$, partially visible), 4.87

5.0 )6-H, s), 4.87 (10-H$_2$, u), 3.68 (13-H$_2$, s).

Step B: Benzhydryl ester of 3-carbamoyloxymethyl-7-methoxy-7β-thiophenoxyacetamido-3-cephem-4-carboxylic Acid By following substantially the procedure described in Example 4, Step B, and by substituting the di-benzhydryl ester of 7β-[(D-5-trichloroethoxycarbonylamino-5-carboxyvaleryl)thiophenoxyamido]-3-carbamoyloxymethyl-7-methoxy-3-cephem-4-carboxylic acid in place of the di-benzhydryl ester of 7β-[(D-5'-trichloroethoxycarbonylamino-5'-carboxyvaleryl)-2-furylacetylamino]-3-carbamoyloxymethyl-7-methoxy-3-cephem-4-carboxylic acid there is obtained, after chromatographic purification, substantially pure product which appears as a single spot on thin layer chromatography (TLC). The IR is in accord with the structure.

UV: λmax. 274μm ε 11350
NMR: (Solvent — CDCl$_3$) δ=3.34 (—OCH$_3$, s), 3.24 (2-H$_2$, partially visible), 5.0 (6-H, s), 4.88 (10-H$_2$, d), 3.68 (13-H$_2$, s).

Step C: 3-Carbamoyloxymethyl-7-methoxy-7β-thiophenoxyacetamido-3-cephem-4-carboxylic Acid The title compound is prepared from the product of Step B above following the procedure of Example 3, Step C. The product exhibits a single spot on TLC. MP: 119°–123° C.

UV: (pH 7 buffer) λmax. 247μm ε 10400
NMR: (Solvent — CD$_3$CN + D$_2$O) δ=3.38 (—OCH$_3$, s), 3.34 (2-H$_2$, partially visible), 5.0 (6-H, s), 4.82 (10-H$_2$, s), 3.71 (13-H$_2$, s).

EXAMPLE 6

7β-(D,L-α-azidophenylacetylamido)-3-carbamoyloxymethyl-7-methoxy-3-cephem-4-carboxylic Acid

Step A: 7β-(D-5-tert-butoxycarbonylamino-5-carboxyvaleramido)-3-carbamoyloxymethyl-7-methoxy-3-cephem-4-carboxylic Acid 7β-(D-5-amino-5-carboxyvaleramido)-3-carbamoyloxymethyl-7-methoxy-3-cephem-4-carboxylic acid (50.0 g.) is dissolved in a mixture of 1500 ml. aqueous 5% dipotassium hydrogen phosphate and 1000 ml. acetone and adjusted to pH 9.5 with 2.5 N sodium hydroxide solution. To this stirred solution is added tert-butoxycarbonyl azide (50 ml.) and the pH maintained at 9.5 over a 20 hour period. The reaction mixture is then extracted with ethyl acetate, the ethyl acetate layer discarded, and the aqueous layer is cooled to 0° C., stirred with 1200 ml. of ethylacetate, and acidified to pH 2.5 with concentrated hydrochloric acid. The ethyl acetate layer is separated, dried over sodium sulfate and concentrated in vacuo, and the solid so obtained may be used without further purification.

IR: 1790 (β-Lactam), 1700
UV: (pH 7 buffer) λmax. 263 ε 6820
NMR: (Solvent — DMSO, d$_6$) δ=3.30 (—OCH$_3$, s), 3.42 (2-H$_2$, partially visible), 5.06 (6-H, s), 4.78 (10-H, d), 1.38 (t-Bu, s).

Step B: Di-benzhydryl ester of 7β-(D-5-tert-butoxycarbonylamino-5-carboxyvaleramido)-3-carbamoyloxymethyl-7-methoxy-3-cephem-4-carboxylic Acid To a solution of 7β-(D-5-butoxycarbonylamino-5-carboxyvaleramido)-3-carbamoyloxymethyl-7-methoxy-3-cephem-4-carboxylic acid (15.0 g.) in ethyl acetate (500 ml.) is added diphenyldiazomethane (5.5 g.) in 70 ml. of ether. The reaction mixture is warmed to 40° C. with stirring and after 30 minutes is treated with additional diphenyldiazomethane (5.5 g.) in ether (70 ml.). After 3 hours, the solvent is removed in vacuo and replaced by a mixture of methanol (500 ml.) and water (20 ml.). The methanol-water solution is extracted four times with hexane and then evaporated in vacuo. The residue is dissolved in ethyl acetate, dried over sodium sulfate and evaporated in vacuo to yield the title compound which is used without purification in the next step.

NMR: (Solvent — CDCl$_3$) δ=3.60 (—OCH$_3$, s), 3.4 (2-H$_2$, partially visible), 5.10 (6-H, s), 4.95 (10-H, partially visible).

Step C: Di-benzhydryl ester of 7β-[(D-5'-tert-butoxycarbonylamino-5'-carboxyvaleryl)-D,L-α-azidophenylacetylamino]-3-carbamoyloxymethyl-7-methoxy-3-cephem-4-carboxylic Acid A mixture of the di-benzhydryl ester of 7β-(D-5'-tert-butoxycarbonylamino-5'-carboxyvaleramido)-3-carbamoyloxymethyl-7-methoxy-3-cephem-4-carboxylic acid (10.8 g.), chloroform (100 ml.), bis-(trimethylsilyl)-trifluoroacetamide (16.2 g.) and D,L-α-azido-phenylacetyl chloride is warmed at 45° C. for 16 hours. The mixture is diluted with chloroform (300 ml.), washed with 2% aqueous bicarbonate and saturated aqueous sodium chloride, dried over sodium sulfate and evaporated to an oil which is purified by precipitating the product from a chloroform solution with hexane. The light yellow solid is used in the next step without further purification.

IR: 1790 (β-Lactam, 1, 1735, 2100 (—N$_3$)

NMR: (Solvent — CDCl$_3$) δ=3.70 (—OCH$_3$, s), 3.2 (2-H$_2$, partially visible).

Step D:
7β-(D,L-α-azidophenylacetylamido)-3-carbamoyloxymethyl-7-methoxy-3-cephem-4-carboxylic Acid A solution of the di-benzhydryl ester of 7β-[(D-5'-tert-butoxycarbonylamino-5'-carboxyvaleryl)-D,L-α-azidophenylacetyl-amino]-3-carbamoyloxymethyl-7-methoxy-3-cephem-4-carboxylic acid (13.0 g.) in anisole (13 ml.) is poured into 65 ml. of cold (0° C.) trifluoroacetic acid. After 5 minutes the solution is poured into 1800 ml. of stirred, cold (0° C.) ether. The precipitated solid is collected and distributed between 10% aqueous disodium acid phosphate and ethyl acetate. The ethyl acetate layer is discarded and the aqueous layer is layered with fresh ethyl acetate and the stirred mixture brought to pH 2 in the cold with 60% aqueous phosphoric acid. The ethyl acetate layer is collected, washed with saturated aqueous sodium chloride and then dried over sodium sulfate. Volatiles are removed in vacuo to afford the title compound.

UV: λmax.
264μm ε 7537
231μm ε13567
(pH 7 buffer)

IR: 1760 (β-Lactam) 1705, 2105 (—N$_3$)

NMR: (Solvent — CD$_3$CN) δ=3.36 (—OCH$_3$, s), 3.50 (—OCH$_3$, s), 3.40 (2-H$_2$, partially visible), 5.06 (6-H, s), 4.86 (10-H, s), 5.15 (13-H, s).

EXAMPLE 7
7β-(D,L-α-aminophenylacetylamido)-3-carbamoyloxymethyl-7-methoxy-3-cephem-4-carboxylic Acid A slurry of 1.0 g. of 7β-(D,L-α-azidophenylacetylamido)-3-carbamoyloxymethyl-7-methoxy-3-cephem-4-carboxylic acid in acetic acid (10 ml.) and water (90 ml.) at 0° C. is stirred with zinc dust (5.0 g.) for 10 minutes and filtered. The filtrate is sparged with hydrogen sulfide, filtered, and the filtrate freeze dried to afford a white solid which is washed with ether and dried in vacuo to afford the title compound as a white powder.

UV: (pH 7 buffer) λmax. 264μm ε 6525

IR: 1770 (β-Lactam) 2650, 1550 (HN$_3$+)

NMR: (Solvent — D$_2$O + HCO$_3$-) δ=3.78 (—OCH$_3$, s), 3.84 (—OCH$_3$, s), 3.90 (2-H$_2$, partially visible).

EXAMPLE 8
3-Acetoxymethyl-7β-(2-thienylacetamido)-3-cephem-4-carboxylic Acid

Step A:
7β-(D-5-Trichloroethoxycarbonylamino)-5-carboxyvaleramido)-3-acetylmethyl-3-cephem-4-carboxylic Acid To a solution of 7β-(D-5-amino-5-carboxyvaleramido)-3-acetoxymethyl-3-cephem-4-carboxylic acid (2.5 g., 0.53 mole) in acetone (13 ml.) and aqueous 10% dipotassium hydrogen phosphate (40 ml.) is added dropwise trichloroethoxycarbonyl chloride (3.35 g., 0.159 mole). During the addition the pH of the solution is kept in the range of from 8.5 to 9 by the gradual addition of a 17% aqueous solution of sodium hydroxide. After 30 minutes the mixture is washed with ethyl acetate and the aqueous layer is acidified to pH 2.5 with concentrated hydrochloric acid. The precipitated product is extracted into ethyl acetate, the solution is dried over sodium sulfate, filtered and the solvent removed to afford 2.7 g. of 7β-(D-5-trichloroethoxycarbonylamino-5-carboxyvaleramido)-3-acetylmethyl-3-cephem-4-carboxylic acid.

Step B: Dibenzhydryl ester of 7-(D-5-trichloroethoxycarbonylamino-5-carboxyvaleramido)-3-acetoxymethyl-3-cephem-4-carboxylic Acid To a solution of 6β-(D-5-trichloroethoxycarbonylamino-5-carboxyvaleramido)-3-acetylmethyl-3-cephem-4-carboxylic acid in ethyl acetate (30 ml.) is added diphenyl diazomethane (2.0 g.) in ether (25 ml.). The mixture is stirred overnight and the solvent removed to afford 4.0 g. of crude product. The crude product is purified by chromatography on silica gel using chloroform as the eluant to afford 2.3 g. of substantially pure dibenzhydryl ester of 7-(D-5-trichloroethoxycarbonylamino-5-carboxyvaleramido)-3-acetylmethyl-3-cephem-4-carboxylic acid.

NMR: (Solvent — CDCl$_3$) δ=2.0 (methyl, s), 4.9 (10-H$_2$, quartet), 3.2 (2-H$_2$, quartet), 4.95 (6-H, d), 5.92 (7-H), 7.0 (benzhydryl protons, 2 s).

Step C: Dibenzhydryl ester of 7-[(D-5-trichloroethoxy-carbonylamino-5-carboxyvaleryl)-2-thienylacetylamino]-3-acetoxymethyl-3-cephem-4-carboxylic Acid A mixture of the dibenzhydryl ester of 7β-(D-5-trichloroethoxycarbonylamino-5-carboxyvaleramido)-3-acetoxymethyl-3-cephem-4-carboxylic acid (2.0 g., 0.02 mole), N-trimethylsilyl trifluoroacetamide (1.65 g., 0.09 mole), 2-thienylacetyl chloride (1.31 g., 0.0815 mole) and methylene chloride (6 ml.) is warmed at 40°-45° C. in an oil bath under a nitrogen atmosphere for 20 hours. The reaction mixture is poured into hexane (100 ml.) and filtered through diatomaceous earth. Removal of the solvent affords the dibenzhydryl ester of 7-[D-5-trichloroethoxycarbonylamino-5-carboxyvaleryl)-2-thienylacetylamino]-3-acetoxymethyl-3-cephem-4-carboxylic acid.

Step D: Benzhydryl ester of 3-acetoxymethyl-7-(2-thienylacetamido)-3-cephem-4-carboxylic Acid The dibenzhydryl ester of 7-[(D-5-trichloroethoxycarbonylamino-5-carboxyvaleryl)-2- thienylacetylamino]-3-acetoxymethyl-3-cephem-4-carboxylic acid is dissolved in ethyl acetate (10 ml.) and added to a mixture of 90% aqueous acetic acid (10 ml.) and zinc dust (1.0 g.). The mixture is stirred for two hours at room temperature. The reaction mixture is filtered to remove the zinc. The reaction mixture is washed successively with 2 portions of water, a cold sodium bicarbonate solution and then with a saturated sodium chloride solution (15.0 ml.). The ethyl acetate solution is dried over sodium sulfate, filtered and the solvent removed to afford 1.9 g. of crude product which is chromatographed on silica gel using a mixture of chloroform and ethyl acetate (50:1) as the eluant to afford 0.380 g. of product which, after recrystallization from ethyl acetate, has a melting point of 141.5°–143° C.

UV: ($CH_3OH$) λmax. 263 ε7580

Elemental analysis for $C_{29}H_{26}N_2O_6S_2$:

Calc.: C, 61.91; H, 4.66; N, 4.98; Found: C, 62.14; H, 4.84; N, 4.91.

Step E:
3-(Acetoxymethyl)-7-(2-thienylacetamido)-3-cephem-4-carboxylic Acid

A cold solution of benzhydryl ester of 3-acetoxymethyl-7-(2-thienylacetamido)-3-cephem-4-carboxylic acid (100 mg.) in anisole (1.0 ml.) and trifluoroacetic acid (0.5 ml.) is stirred at 0° C. for 35 minutes. Carbon tetrachloride (50 ml.) is added and the reaction mixture is concentrated to dryness. The residue is triturated with hexane. The hexane is removed by decantation and this residue is dissolved in ethyl acetate (10 ml.), concentrated to 1 ml. and diethyl ether added to afford precipitate. This precipitate is recrystallized from a mixture of diethyl ether and ethyl acetate to afford 0.025 g. of 3-(acetoxymethyl)-7-(2-thienylacetamido)-3-cephem-4-carboxylic acid, m.p. 164° C. Mixed melting point with an authentic sample was 163° C.

EXAMPLE 9

7-(Trifluoroacetyl)amino-3-carbamoyloxymethyl-7-methoxy-3-cephem-4-carboxylic acid A. Dibenzhydryl ester of 7-[N-trifluoroacetyl-6S'-(trichloroethoxycarbonylamino-5'-carboxy)valeramido]-3-carbamoyloxymethyl-7-methoxy-3-cephem-4-carboxylic acid A mixture of dibenzhydryl ester of 7-(D-5'-trichloroethoxycarbonylamino-5'-carboxyvaleramido)-3-carbamoyloxymethyl-7-methoxy-3-cephem-4-carboxylic acid (2.0 g., 2.1 mm.), trifluoroacetyl chloride (4.0 g., 30.0 mm.), methylene chloride (10 ml.) and N-trimethylsilyl trifluoroacetamide (5 ml., 32 mm.) is placed in a tube, sealed and allowed to stand at room temperature for 21 hours. After this period, the volatile products are removed under vacuum to give 6.5 g. of crude material. The product, dibenzhydryl ester of 7-[N-trifluoroacetyl-6S'-(trichloroethoxycarbonyl-amino-5'-carboxy)-valeramido]-3-carbamoyloxymethyl-7-methoxy-3-cephem-4-carboxylic acid, so obtained is used directly in the following step.

B. Benzhydryl ester of 7-(trifluoroacetylamino)-3-carbamoyloxymethyl-7-methoxy-3-cephem-4-carboxylic acid A solution of imide obtained in A above (6.5 g.) in anhydrous acetonitrile (40 ml.) is stirred with activated zinc dust (10 g.) and acetic acid (2.0 ml.) for 1 hour. The resulting mixture is filtered and the zinc pad washed with methylene chloride. The filtrate is concentrated to dryness and the residue chromatographed on silica gel (60 g.) and eluted with chloroform-hexanemethanol (50:50:2) to give the title compound. IR: 1800, 1750 ($CH_2Cl_2$). NMR is in accord with the structure.

C. 7-(Trifluoroacetyl)amino-3-carbamoyloxymethyl-7-methoxy-3-cephem-4-carboxylic acid A cold solution (0-4° C.) of dioxane (0.04 ml.), methylene chloride (0.27 ml.) and trifluoroacetic acid (0.27 ml.) is added to a cold solution (0-4° C.) of anisole (0.19 ml.), methylene chloride (0.52 ml.) and the product of B (100 mg.). The reaction is allowed to continue for 40 minutes at 0–4° C. After this period, the reaction is quenched by the addition of dioxane (1ml.) and carbon tetrachloride (10 ml.) and then concentrated to dryness. The residue is triturated with hexane to give the title compound. IR: 1800, 1740 ($CH_3CN$). NMR is in accord with the structure.

EXAMPLE 10

Benzhydryl 3-carbamoyloxymethyl-7-methoxy-7-trifluoroacetamido-3-cephem-4-carboxylic acid A mixture of the dibenzhydryl ester of 7β-(D-5'-trichloroethoxycarbonylamino-5'-carboxyvaleramido)-3-carbamoyloxymethyl-7-methoxy-3-cephem-4-carboxylic acid (5g), trifluoroacetic anhydride (1.4 ml. ), trimethylsilyl trifluoroacetamide (2.25 g.) and methylene chloride (20 ml.) is heated to 40° C. for 3 hours. The mixture is poured into hexane and the precipitate dissolved in acetonitrile. To this solution is added acetic acid (4 ml.) and zinc powder (25 g.) and the mixture is agitated for 3 hours. After filtration the solvent is removed and the residue chromatographed on silica gel (100 g.) using a mixture of benzene and ethyl acetate for elution. The titled product is obtained as a white foam which exhibits the expected NMR spectra.

EXAMPLE 11

3-Carbamoyloxymethyl-7-methoxy-7β-(2-thienylacetamido)-3-cephem-4-carboxylic acid A. Di(methozymethyl) 3-carbamoyloxymethyl-7-methoxy-7β-(D-5-trichloroethoxycarbonylamino-5'-carboxyvaleramido)-3-cephem-4-carboxylate To a cold suspension of di(cyclohexylamine) 3-carbamoyloxymethyl-7-methoxy-7-(2-thienylacetamido)-3-cephem-4-carboxylate (9.85 g.) in methylene chloride (dried over molecular sieves, 170 ml.) at 0° C. is added a solution of chloromethyl methyl ether (1.69 g.) in 50 ml. of methylene chloride dropwise over 60 minutes with stirring. After the addition, the suspension is stirred at 0° C. for 2 hours. The mixture is filtered through a pad of celite and the pad rinsed with methylene chloride (30 ml. × 3). The filtrate is evaporated to dryness in vacuo at 5°-10° C. and the residue shaken with 200 ml. methylene chloride and 200 ml. ice water. The organic layer is separated, washed further with ice water (200 ml.), cold 0.1% $NaHCO_3$ solution (200 ml.), water (200 ml.), and 50 ml. aqueous NaCl solution and dried over magnesium sulfate. After filtering off the drying agent the solvent is removed in vacuo to give 6.25 g. of product as a glass.

B. Di(methoxymethyl) 3-carbamoyloxymethyl-7-methoxy-7β-[(D-5'-trichloroethoxycarbonylamino-5'-carboxyvaleryl)-thienylacetylamino]-3-cephem-4-carboxylate To a solution of di(methoxymethyl) 3-carbamoyloxymethyl-7-methoxy-7β-(D-5-trichloroethoxycarbonylamino-5'-carboxyvaleramido)-3-cephem-4-carboxylate in 80 ml. of sieve dried methylene chloride is added α-pinene (13.5 ml.), N-trimethylsilyl ethylurethane (12.1 ml.) and 2-thienylacetyl chloride (7.0 ml.). The solution is aged 17 hours under a dry nitrogen atmosphere while gently refluxing in a 50° C. oil bath. The solution is then cooled to room temperature, treated with 500 ml. of an aqueous solution containing 10% sodium chloride and 2.5% sodium bicarbonate, methanol (30 ml.) added and the mixture agitated vigorously for 15 minutes at ambient temperature. The layers are separated, the aqueous layer backwashed with methylene chloride (20 ml.), the combined methylene chloride layers washed with saturated aqueous sodium chloride (30 ml.), the sodium chloride solution backwashed with methylene chloride (30 ml.) and the combined methylene chloride solutions dried over magnesium sulfate, filtered and the cake washed with 2 × 3 cake volumes of methylene chloride. The combined methylene chloride solution and washes are concentrated in vacuo to 50 ml., quenched dropwise onto vigorously stirred ice cold hexane (500 ml.), and after settling 15 minutes the hexane layer is decanted from the gummy solid by filtering through celite pad. The gummy solid and pad are washed with ≈50 ml. hexane, then the celite pad washed with 50 ml. methylene chloride and this methylene chloride solution used to dissolve the gummy solid. The methylene chloride solution is then placed through the hexane precipitation again. The product, di(methoxymethyl) 3-carbamoyloxymethyl-7-methoxy-7β-[(D-5'-trichloroethoxycarbonylamino-5'-carboxyvaleryl)thienylacetylamino]-3-cephem-4-carboxylate, is dissolved in 230 ml. of ethyl acetate and used in the next step.

C. Di(methoxymethyl) 3-carbamoyloxymethyl-7-methoxy-7β-(2-thienylacetamido)-3-cephem-4-carboxylate The ethyl acetate solution is charged to a 500 ml. 3-neck round bottom flask fitted with a thermometer mechanical stirrer and a nitrogen line. Zinc dust (50.6 g.) is charged and the solution is stirred while 11.5 l ml. glacial acetic acid are added. After all the reagents are charged, the reaction is run under a nitrogen atmosphere at 25° C. for 1 hour. The zinc is filtered off and washed with ethyl acetate (2 × 75 ml.). The filtrate is washed with 2 × 150 ml. of water and once with cold 2.5% sodium bicarbonate (150 ml.) followed by one wash 100 ml. of saturated sodium chloride. The ethyl acetate solution is dried over sodium sulfate, filtered and concentrated to obtain the product as a gum.

Into a cooled (0°-4° C. ) jacketed column (2.5 cm. inner diameter) is charged a slurry of 64 g. of silica gel (60–200 mesh) in methylene chloride (200 ml.). The silica gel is allowed to settle and the excess methylene chloride drained off to the level of the bed. To this is charged 6.4 g. of the residue in a minimum amount of methylene chloride (5–10 ml.), the flask and column walls being washed with methylene chloride (10 ml.) and then the column eluted with 2 liters of 40% ethyl acetate-benzene solution taking 60 ml. fractions. The fractions are then concentrated to dryness. Fractions 10–18 containing the product are evaporated to obtain 2.9 g. of di(methoxymethyl) 3-carbamoyloxymethyl-7-methoxy-7β-(2-thienylacetamido)-3-cephem-4-carboxylate.

The product (2.64 g.) is dissolved in methylene chloride (150 ml.) and filtered. To this solution is added ethanol (20 ml.) and concentrated at room temperature on a rotary evaporator to a volume of about 20 ml. An additional 20 ml. of ethanol is added to this volume and concentrated to about 30 ml. The solution is seeded and allowed to crystallize to give 2.1 g. of pure ester. m.p. = 151°–153° C.

D. 3-Carbamoyloxymethyl-7-methoxy-7β-(2-thienylacetamido)-3-cephem-4-carboxylic acid A suspension of the methoxymethyl ester (920 mg.) in 9.2 ml. of methanol (containing 10% concentrated HCl) is stirred at room temperature for 50 minutes. The completeness of reaction is ascertained by tlc analysis, using ethyl acetate/benzene 6:4 system. A cold solution of 1.65 g. NaHCO₃ in 40 ml. of water is added cautiously and the clear solution concentrated to a volume of 30-35 ml. at room temperature in vacuo. The aqueous solution is extracted with ethyl acetate to remove neutral impurities and the organic layer discarded. The aqueous layer is cooled to 0°-5° C., covered with ethyl acetate (40 ml.) and the pH adjusted to 1.8 with cold 10% HCl with constant stirring. The layers are separated and the ethyl acetate layer washed 3 × 3 ml. ice water. The aqueous layer and washing are combined and then re-extracted with 2 × 20 ml. ethyl acetate. The second ethyl acetate extract is washed twice with cold water and combined with the first extract. The solvent is evaporated to dryness and flushed with 10 ml. of benzene-methanol (8:2) and dried to constant weight. Recrystallization of the crude product from methanol/ethyl acetate affords 3-carbamoyloxymethyl-7 -methoxy-7β-(2-thienylacetamido)-3-cephem-4-carboxylic acid.

EXAMPLE 12

3-Carbamoyloxymethyl-7-methoxy-7β-(2-thienylacetamido)-3-cephem-4-carboxylic acid

A. 3-Carbamoyloxymethyl-7-methoxy-7β-[D-5-(2-nitrophenyl-sulfenylamino)-5-carboxyvaleramido]-3-cephem-4-carboxylic acid The monosodium salt of 3-carbamoyloxymethyl-7-methoxy-7β-(D-5'-amino-5'-carboxyvaleramido)-3-cephem-4-carboxylic acid (0.37 g.) is dissolved in 15 ml. of water. Dioxane (30 ml.) is added, followed by enough sodium hydroxide to adjust the pH to 8.5–9.0. 2-Nitrophenylsulfenyl chloride (0.55 g.) is added to the reaction over 20 minutes simultaneously with aqueous sodium hydroxide, maintaining the pH between 8.5–9.0. After stirring the reaction for an additional 30 minutes, 45 ml. of water is added, the mixture filtered, and the filtrate extracted with 25 ml. of ethyl acetate. The aqueous layer is cooled to 0°-5° C., acidified with concentrated hydrochloric acid, and the product extracted into ethyl acetate. The ethyl acetate layer is washed with water, dried over sodium sulfate, filtered, and concentrated to give the titled product; weight 0.60 g.

B. Bis-dicyclohexylamine salt of 3-carbamoyloxymethyl-7β-[D-5-(2-nitrophenylsulfenylamino)-5-carboxyvaleramido]-3-cephem-4-carboxylic acid 3-Carbamoyloxymethyl-7-methoxy-7β-[D-5-(2-nitrophenylsulfenylamino)-5-carboxyvaleramido]-3-cephem-4-carboxylic acid is dissolved in 25 ml. of ethyl acetate, filtered, and the filtrate is treated over 15 minutes with 0.675 g. of dicyclohexylamine acetate salt dissolved in 100 ml. of ethyl acetate. Precipitates are collected on a funnel, washed with 10 ml. of ethyl acetate, followed by 2 × 10 ml. of isopropyl ether, then dried in vacuo to give 0.38 g. of the abovetitled salt.

C. Di-methoxymethyl ester of 3-carbamoyloxymethyl-7β-[D-5-(2-nitrophenylsulfenylamino)-5-carboxyvaleramido]-3-cephem-4-carboxylic acid To a solution of 0.25 g. of the bis-dicyclohexylamine salt in 5 ml. of methylene chloride under nitrogen is added 0.045 ml. of chloromethyl methylether in 1.5 ml. of methylene chloride over 15 minutes while maintaining the temperature of the reaction at 5° C. After 4 hours at 0-5° C. the reaction is filtered and the filtrate washed with 2 ml. of water containing 25 mgs. of sodium bicarbonate. The methylene chloride layer is dried over sodium sulfate, filtered, and concentrated to 0.155 g. of crude product. The crude diester is dissolved in 0.5 ml. of a mixture of ethyl acetate-benzene (1:1) and chromatographed on 0.75 g. of silica gel employing the same solvent mixture to give 0.144 g. of the titled product.

D. Di-methoxymethyl ester of 3-carbamoyloxymethyl-7β-[D-5-(2-nitrophenylsulfenylamino)-5-carboxyvaleryl)-(2-thienylacetyl)amino]-3-cephem-4-carboxylic acid To a solution of 0.345 g. of di-methoxymethyl ester of 3-carbamoyloxymethyl-7β-[D-5-(2-nitrophenylsulfenylamino)-5-carboxyvaleramido]-3-cephem-4-carboxylic acid in 3 ml. of chloroform (alcohol free) is added 0.477 ml. of pinene, 0.430 ml. of N-trimethylsilyl-urethane, and 0.248 ml. of thienylacetyl chloride and the mixture stirred for 23 hours at room temperature. The reaction mixture is added to 50 ml. of hexane to give a precipitate. The hexane is decanted and the precipitate washed with 10 ml. of hexane and then dissolved in 3 ml. of dry methylene chloride and re-precipitated by addition to 50 ml. of hexane to give 0.252 g. of crude product. The crude product is chromatographed over 2.5 g. of silica gel employing ethyl acetate-benzene (1:1) to give 0.106 g. of the titled product.

E. 3-Carbamoyloxymethyl-7-methoxy-7β-(2-thienylacetamido)-3-cephem-4-carboxylic acid A solution of 10 mg. of the dimethoxymethyl ester prepared in D above in 0.15 ml. of methanol is treated with 0.05 ml. of acetic acid and 10 mg. of thioacetamide to give the methoxymethyl ester after 5 minutes. When the reaction time is extended to 30 minutes, the titled product is formed by loss of the methoxymethyl ester grouping.

Other reagents than thioacetamide which are known in the art to cleave the nitrophenylsulfenyl group such as thiourea, sulfurous acid, thiourethane, sodium thiosulfate, thiophenol, thioglycolic acid, hydrogen sulfide, and ammonium thiocyanate can be used in place of thioacetamide.

EXAMPLE 13

3-Carbamoyloxymethyl-7-methoxy-7β-(2-thienylacetamido)-3-cephem-4-carboxylic acid When 2,4-dinitrophenylsulfenyl chloride is substituted for 2-nitrophenylsulfenyl chloride in Example 12A and the remaining steps are carried out as in Example 12B, C, D and E above, the same product is obtained. Thus, these processes are carried out as follows:

A solution of 4.41 g. of the monosodium salt of 3-carbamoyloxymethyl-7-methoxy-7β-(D-5'-carboxyvaleramido)-3-cephem-4-carboxylic acid in 106 ml. water and 244 ml. of dioxane is treated with 8.4 g. of 2,4-dinitrophenylsulfenyl chloride at pH 8.5-9.0 by addition of sodium hydroxide as necessary. After 1 hour the reaction is diluted with 350 ml. of water, filtered, and the filtrate extracted with 1 × 175 ml. of ethyl acetate. The aqueous layer is cooled to 0°-5° C., 175 ml. of ethyl acetate added, and the pH adjusted to 2.2 concentrated HCl. The ethyl acetate layer is washed with water, dried over sodium sulfate, filtered, and concentrated in vacuo to 8.52 g. of product.

The N-(2,4-dinitrophenylsulfenyl) compound (8.5 g.) in 195 ml. of ethyl acetate is treated with 6.8 g. of dicyclohexylamine acetate salt in 700 ml. of ethyl acetate. After 45 minutes the product salt is collected and washed with 100 ml. of ethyl acetate, then 3 × 20 ml. of isopropyl ether. After drying in vacuo the product weighs 8.7 g.

A suspension of 8.0 g. of N-(2,4-dinitrophenylsulfenyl)dicyclohexylamine salt in 128 ml. of methylene chloride is treated at 0° C. over 25 minutes with 1.5 ml. of chloromethyl methyl ether in 51 ml. of methylene chloride. After 2 hours the reaction mixture is filtered and the filtrate washed with 200 ml. of ice water, 200 ml. of cold saturated sodium bicarbonate, 2 × 200 ml. of ice water, 200 ml. of cold saturated sodium chloride, then dried over sodium sulfate, filtered, and concentrated to 5.14 g. of crude product ester. The product is dissolved in 25 ml. of ethyl acetate and filtered through a 52 g. of silica gel bed, then concentrated in vacuo to afford 4.72 g. of purified ester.

A solution of 0.50 g. of N-(2,4-dinitrophenyl-sulfenyl)dimethoxy methyl ester in 4 ml. of methylene chloride is treated with 0.652 ml. of α-pinene, 0.586 ml. of N-trimethylsilyl-urethane, and 0.338 ml. of thienylacetyl chloride at reflux temperature for 17 hours, after which the reaction is poured into 50 ml. of ice cold hexane to give a solid which is re-precipitated from ice cold hexane to give 0.606 g. of the diacylated product.

20.1 Mg. of the diacylated product in 0.47 ml. of acetic acid is treated with 23.2 mg. of thiourea for 95 minutes to give 3-carbamoyloxymethyl-7-methoxy-7β-(2-thienylacetamido)-3-cephem-4-carboxylic acid directly as observed by thin layer chromatography comparison with an authentic sample of the same product.

EXAMPLE 14

3-Carbamoyloxymethyl-7-methoxy-7β-(2-thienylacetamido)-3-cephem-4-carboxylic acid

A. Di-benzyloxymethyl ester of 3-carbamoyloxymethyl-7-methoxy-7β-(D-5-trichloroethoxycarbonylamino-5-carboxyvaleramido)-3-cephem-4-carboxylic acid A suspension of 985 mg. of the bis-dicyclohexylamine salt of 3-carbamoyloxymethyl-7-methoxy-7β-(D-5-trichloroethoxycarbonylamino-5-carboxyvaleramido)-3-cephem-4-carboxylic acid in 17 ml. of methylene chloride at 0°–1° C. is treated with 0.294 ml. of chloromethyl benzyl ether in 5 ml. of methylene chloride by addition over 52 minutes. After 4 hours the reaction is filtered and the filtrate treated with 2 × 5 ml. of cold saturated sodium bicarbonate, 2 × 10 ml. of ice water, then dried over sodium sulfate and filtered. The filtrate is concentrated to a residue, then slurried with 15 ml. of isopropyl ether and the titled product as a solid collected on a funnel (726 mg.).

B. Di-benzyloxymethyl ester of 3-carbamoyloxymethyl-7-methoxy-7β-[D-5-trichloroethoxycarbonylamino-5-carboxyvaleryl-(2-thienylacetyl)amino]-3-cephem-4-carboxylic acid A solution of 0.20 g. of the di-benzyloxymethyl ester in 1.6 ml. of methylene chloride is treated with 0.222 ml. of α-pinene, 0.20 ml. of N-trimethylsilylurethane, and 0.115 ml. of 2-thienylacetyl chloride at reflux temperature for 23 hours. The reaction mixture is extracted with 2 ml. of an ice cold solution containing 2.5% sodium bicarbonate and 10% sodium chloride and the methylene chloride solution washed with 2 ml. of saturated sodium chloride solution, dried over magnesium sulfate, filtered, and the filtrate added to 50 ml. of cold hexane to give the titled product as a precipitate; weight 0.161 g.

C. Benzyloxymethyl 3-carbamoyloxymethyl-7-methoxy-7β-(2-thienylacetamido)-3-cephem-4-carboxylate A solution of the imide prepared in B above (0.150 g.) in 4.1 ml. of dioxane containing 0.20 ml. of acetic acid is treated with 0.86 g. of activated zinc for 2½ hours. The reaction is filtered and the residue on the funnel washed with 20 ml. of chloroform. The combined filtrate is washed with 2 × 20 ml. of water, 10 ml. of cold saturated sodium bicarbonate, 10 ml. of saturated sodium chloride, then dried over magnesium sulfate, filtered, and concentrated to give 0.143 g. of residue containing the benzyloxymethyl ester.

D. 3-Carbamoyloxymethyl-7-methoxy-7β-(2-thienylacetamido)-3-cephem-4-carboxylic acid 25.4 Mg. of the benzyloxymethyl ester is dissolved in 0.25 ml. of a solution made from 9 ml. of methanol and 1 ml. of concentrated hydrochloric acid. After 1 hour the reaction is complete and the product is isolated by concentration in vacuo.

EXAMPLE 15

Methoxymethyl ester of 3-Carbamoyloxymethyl-7-methoxy-7β-(2-thienylacetamido)-3-cephem-4-carboxylic acid

A. 7-(D-5-chloroacetamidoadipamido)-7-methoxy-3-carbamoyl-oxymethyl-3-cephem-4-carboxylic acid The monosodium salt of 7β-(D-5-amino-5-carboxyvaleramido)-3-carbamoyloxymethyl-7-methoxy-3-cephem-4-carboxylic acid (14.2 g., 63.6% pure) is dissolved in 200 ml. of an ice cold aqueous solution of 4.9 ml. of 85% $H_3PO_4$ (adjusted to pH 7.0 with 50% NaOH) contained in a cold jacketed Waring blender. A pH electrode is suspended in the solution and, with maximum agitation, the pH is adjusted to 11.0. A 4.0 ml. aliquot of freshly distilled chloroacetyl chloride is added and the pH maintained at 10.5–11.0 by NaOH addition. Additional acid chloride (4.0 ml., then 2.0 ml.) is charged in the same manner and after 10 minutes maximum agitation the conversion to the title compound is judged complete by thin layer chromatography.

The reaction mixture is stirred with an equal volume of ethyl acetate and acidified with concentrated HCl to pH 1.7 at 0° C. The layers are separated and the extraction repeated with four additional volumes of ethyl acetate containing 1 ml. each of acetic acid. The combined extracts are dried over $Na_2SO_4$, concentrated in vacuo and the yellow, oily residue precipitated from 300 ml. of benzene. The crude title compound (5.35 g., 51%, ca 60% pure) is collected by centrifugation.

B. Bis-methoxymethyl ester of 3-carbamoyloxymethyl-7-methoxy-7-(D-5-chloroacetamidoadipamido)-3-cephem-4-carboxylic acid To 100 ml. of sieve dried methylene chloride is added 1.35 ml. of sym-collidine and 2.68 g. (5.13 mmol) of the product obtained in A above. The light yellow suspension is cooled to 5° C. under $N_2$ and two 0.335 ml. portions of $ClCH_2OCH_3$ are added with rapid stirring and maintenance of the reaction temperature at 5°–10° C. The mixture is stirred 45 minutes and 10% more of collidine and $ClCH_2OCH_3$ added. After a total of 1.75 hours the mixture is filtered. The filtrate is washed with three 50 ml. portions of ice water, 50 ml. of saturated NaCl solution and dried over $Na_2SO_4$. The filtered extracts are concentrated in vacuo giving 1.80 g. of crude diester which is purified by chromatography on 30 g. of coarse silica gel. Elution with 400–500 ml. of $CH_2Cl_2$ gives by-products and elution with 500 ml. of ethyl acetate gives 1.22 g. of white, amorphous, solid title diester.

C. Methoxymethyl 3-carbamoyloxymethyl-7-methoxy-7β-[D-5-chloroacetamidoadipoyl-(2-thienylacetyl)amino]-3-cephem-4-carboxylate To 100 mg. of the product of B above in a sealed Hypovial is added 0.350 ml. of ethanol-free $CHCl_3$, 0.068 ml. of N-trimethylsilyl-urethane (0.395 mmol), and 2-thienylacetyl chloride (0.034 ml., 0.274 mmol). The homogeneous mixture is heated 4 hours at 50° C. and then allowed to stand 24 hours at room temperature. The reaction mixture is precipitated from 3 volumes of dry hexane and the precipitate collected by centrifugation, dissolved in CH$_2$Cl$_2$, and the solution concentrated in vacuo to a light yellow foam; yield 80 mg. Thin layer chromatography and an nmr spectrum shows this material to be essentially pure title compound.

D. Methoxymethyl ester of 3-carbamoyloxymethyl-7-methoxy-7β-(2-thienylacetamido)-3-cephem-4-carboxylic acid The crude imide obtained in C above (20 mg.) in 0.250 ml. of absolute ethanol is treated with 5 mg. of thiourea for 24 hours at room temperature. The methoxymethyl ester is shown to be present by thin layer chromatography and the starting imide has completely reacted.

Alternatively, the crude imide (25 mg.) and zinc dust (100 mg.) are treated with a mixture of 0.5 ml. of ethyl acetate and 0.025 ml. of glacial acetic acid. After 4 hours at room temperature the presence of the titled product is demonstrated by thin layer chromatography.

EXAMPLE 16

3-Carbamoyloxymethyl-7-methoxy-7β-(2-thienylacetamido)-3-cephem-4-carboxylic acid One-tenth g. of bis-dicyclohexylamine salt of 3-carbamoyloxymethyl-7β-[D-5-(2,4-dinitrophenylsulfenylamino)-5-carboxyvaleramido]-3-cephem-4-carboxylic acid is placed in methylene chloride (3 ml.) and stirred at 25° C. for 2 hours with 26.5 µl. of trimethylsilyl chloride. Dicyclohexylamine hydrochloride (42 mg.) is filtered off and the filtrate treated with 100 µl. of N-trimethylsilyl ethyl carbamate and 43.5 µl. (0.35 mmole) of 2-thienylacetyl chloride. The solution is refluxed for 19 hours. Six ml. hexane is added, the mixture stirred, and the supernatent decanted. This is repeated twice more to remove excess 2-thienylacetyl chloride. 85 Mg. of hexane insoluble material is treated with 50 mg. of thioacetamide in 1 ml. methanol and stirred for 2.5 hours. Ethyl acetate (5 ml.) is added and washed with sodium bicarbonate solution (pH 8.3). The water layer is washed with ethyl acetate and the aqueous layer acidified to pH 2.8 with 17% H$_3$PO$_4$. Product (28 mg.) containing the title product is extracted from the acidic water with ethyl acetate.

EXAMPLE 17

Methoxymethyl 3-carbamoyloxymethyl-7-methoxy-7β-(2-thienylacetamido)-3-cephem-4-carboxylate To a mixture of 6.75 ml. of α-pinene and 12 ml. of dichloroethane is added 5.55 mg. of N-trimethylsilyl benzene sulfonamide, 3.5 ml. of 2-thienylacetyl chloride, and 500 mg. of methoxymethyl 7β-(D-5-trichloroethoxycarbonylamino-5-carboxyvaleramido)-3-carbamoyloxymethyl-7-methoxy-3-cephem-4-carboxylate. The resulting reaction mixture is heated under reflux at 65° C. for 10 hours. 3.4 Ml. of the resulting solution is then cooled in dry ice and then warmed to reflux temperature. The resulting solution containing solid crystals is diluted to 100 ml. with dichloroethane. Assay of the resulting solution indicates the presence of 41.8 mg. of the above-titled product.

EXAMPLE 18

3-Carbamoyloxymethyl-7-methoxy-7β-(2-thienylacetamido)-3-cephem-4-carboxylic acid To a slurry of 200 mg. of 7β-(D-5'-t-butoxycarbonylamino-5'-carboxyvaleramido)-3-carbamoyloxymethyl-7-methoxy-3-cephem-4-carboxylic acid in ethanol-free chloroform (2ml.) is added 432 mg. of N-trimethylsilyl trifluoroacetamide and 0.56 mg. of triethylamine. To this mixture is added 182 µl. of thienylacetyl chloride. The solution is heated in an oil bath to 45° C. for 9½ hours. The mixture is then quenched by adding n-hexane. The solution is centrifuged and the hexane poured off the gummy solid. This procedure is repeated and the hexane fractions discarded. The gummy solid is dissolved in 10 ml. formic acid for 30 minutes. The formic acid is removed in vacuo. The solid is distributed between ethyl acetate (3 ml.), water (3 ml.) and the pH adjusted to 2.5. The ethyl acetate layer is concentrated to dryness. Both TLC analysis and liquid chromatography show the presence of 3-carbamoyloxymethyl-7-methoxy-7β-(2-thienylacetamido)-3-cephem-4-carboxylic acid. The crude product is purified by preparative TLC using silica gel plates and a solvent consisting of benzene 50; methanol 10; acetic acid 6.

EXAMPLE 19

3-Carbamoyloxymethyl-7-methoxy-7β-(2-thienylacetamido)-3-cephem-4-carboxylic acid To a slurry of 200 mg. of 7β-(D-5-amino-5-carboxyvaleramido)-3-carbamoyloxymethyl-7-methoxy-3-cephem-4-carboxylic acid in 2 ml. of ethanol-free chloroform is added 430 mg. of N-trimethysilyl benzenesulfonamide and 0.6 mg. of triethylamine. To this mixture is added 182 µl. of thienylacetyl chloride. The resulting reaction mixture is heated in an oil bath at 45° C. for 10 hours and then quenched by adding to n-hexane. The solution is centrifuged and the hexane discarded from the gummy solid. This procedure is repeated twice more and the hexane fractions are discarded. The gummy solid is distributed between 3 ml. of ethyl acetate and 3 ml. of water, and the pH is adjusted to 2.5. Concentration of the ethyl acetate layer to dryness affords crude 3-carbamoyloxymethyl-7-methoxy-7β-(2-thienylacetamido)-3-cephem-4-carboxylic acid which is characterized by TLC analysis and liquid chromatography. The crude product is purified by preparative TLC using silica gel plates and a solvent system consisting of benzene 50; methanol 10; and acetic acid 6.

EXAMPLE 20

Dibenzylethylenediamine salt of 3-methyl-7-methoxy-7β-(2-thienylacetamido-3-cephem-4-carboxylic Acid

Step A:

7β-(D-5-Amino-5-carboxyvaleramido)-3-methyl-7-methoxy-3-cephem-4-carboxylic Acid A 10% palladium on charcoal catalyst is suspended in water (80 ml.) and treated with hydrogen. The catalyst is filtered and suspended again in water (50 ml.) and to this mixture (2.67 g.) is added the sodium salt of 7β-(D-5-amino-5-carboxyvaleramido)-3-carbamoyloxymethyl-7-methoxy-3-cephem-4-carboxylic acid (1.0 g.) in water (10 ml.). The resulting mixture is shaken for 22 hours at room temperature. The catalyst is removed by filtration and washed with water (50 ml.). The combined wash and filtrate is concentrated to dryness to afford a 52.8% yield of 7β-(D-5-amino-5-carboxyvaleramido)-3-methyl-7-methoxy-3-cephem-4-carboxylic acid (528 mg.).

UV: λmax. 265μm; E 1cm/1% is 100

Step B: Dibenzylethylenediamine salt of 7β-(D-5-tert-butoxycarbonylamino-5-carboxyvaleramido)-7-methoxy-3-methyl-3-cephem-4-carboxylic Acid A solution of the disodium salt of 7β-(D-5-amino-5-carboxyvaleramido)-7-methoxy-3-methyl-3-cephem-4-carboxylic acid (11.5 g.) is dissolved in water (150 ml.) and acetone (50 ml.). The pH is adjusted to 9–9.1 with sodium hydroxide and 10 ml. of tert-butyl azidoformate is added. The reaction mixture is stirred for 16 hours at room temperature with additional sodium hydroxide being added to maintain the pH at 9–9.1. The reaction mixture is extracted with ethyl acetate (100 ml.) and the organic layer discarded. The product is precipitated by lowering the pH to 2.5 with dilute hydrochloric acid. The precipitate is collected by centrifugation and converted to its dibenzylethylenediamine salt which is crystallized from ethyl acetate. There is obtained 4.3 g. of the dibenzylethylenediamine salt of 7β- (D-5-tert-butoxycarbonylamino-5-carboxyvaleramido)-7-methoxy-3-methyl-3-cephem-4-carboxylic acid, m.p. 177°–179° C. (dec.).

UV: λmax. 263μm, 238 $E_{1cm}^{1\%}$ = 98.2, 81.1

Elemental analysis for $C_{36}H_{49}N_5O_9S$:

Calc. C, 59.42; H, 6.74; N, 9.63; Found: C, 60.02; H, 6.80; N, 9.79.

Step C: Dibenzylethylenediamine salt of 3-methyl-7-methoxy-7β-(2-thienylacetamido-3-cephem-4-carboxylic Acid The 7β-(D-5-tert-butoxycarbonylamino-5-carboxyvaleramido)-3-methyl-7-methoxy-3-cephem-4-carboxylic acid is treated with aqueous dilute hydrochloric acid (200 ml., 0.1 N) and ethyl acetate (100 ml.) in order to extract the free acid. To a solution of 1.33 g. (2.74 mmoles) of the free acid in methylene chloride (10 ml.) is added bis-trimethylsilyl trifluoroacetamide (2.2 ml.) and mono-trimethylsilyl trifluoroacetamide (0.5 ml.). 2-Thienylacetyl chloride (1.1 ml.) is then added and the reaction mixture stirred for 18 hours under a nitrogen atmosphere at 43° C. The solvent is removed in vacuo, and the residue partitioned between ethyl acetate and aqueous phosphate buffer (pH 7.5). The aqueous layer is acidified with dilute hydrochloric acid and the precipitated product extracted with ethyl acetate. Addition of dibenzethylenediamine results in crystallization of 250 mg. of the desired product as a salt in the proportion of 2 equivalents of product to one mole of dibenzylethylenediamine. Recrystallization of the salt from ethanol affords substantially pure product, m.p. 153°–155° C. (dec.) with previous darkening.

Elemental analysis for $C_{46}H_{52}S_4N_6O_{10}$:

Calc.: C, 56.54; H, 5.36; N, 8.60; S, 13.12; Found: C, 55.75; H, 5.16; N, 8.37; S, 12.16.

EXAMPLE 21

7-(Phenylacetyl-2-thienylacetyl)amino-3-acetoxymethyl-3-cephem-4-carboxylic Acid A suspension of sodium cephalothin (3.36 g.) in anhydrous alcohol-free chloroform (20 ml.) is silylated by the addition of trimethylchlorosilane (2.2 ml.). After stirring for 30 minutes, monosilyltrifluoroacetamide (5.0 ml.) and phenylacetyl chloride (4.0 ml.) are added and the mixture is then heated to 45° C. for 2 days under a condenser fitted with a drying tube. The volatiles are evaporated to afford a residue which is dissolved in 100 ml. of ethyl acetate and washed three times with water. The ethyl acetate layer is dried over magnesium sulfate, filtered and the solution evaporated in vacuo to a residue. The residue is triturated with chloroform, any insolubles are removed by filtration and the product precipitated from the filtrate with hexane. This procedure is followed two more times. The 7-(phenylacetyl-2-thienylacetyl)amino-3-acetoxymethyl-3-cephem-4-carboxylic acid is obtained in a solvent-free form by freeze drying from a solution in benzene.

IR: (CHCl₃) 1780μ 1720μ

NMR: (CDCl₃) — Consistent with structure;

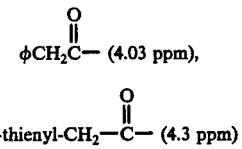

TLC: 1 major spot, $R_f$=0.69 (EtOAC:62, $C_5H_5N$:21, HOAC:6, H₂O:11) on silica gel.

EXAMPLE 22

7-(Di-2-thienylacetyl)amino-3-acetoxymethyl-3-cephem-4-carboxylic Acid

A suspension of sodium cephalothin (1.18 g.) in anhydrous alcohol-free chloroform (10 ml.) is silylated by the addition of trimethylchlorosilane (1.1 ml.). After stirring for 30 minutes, monosilyltrifluoroacetamide (2.5 ml.) and 2-thienylacetyl chloride (2.0 ml.) are added to the suspension which is then heated to 45° C. The mixture is allowed to remain at this temperature for two days and then evaporated in vacuo to a residue which is dissolved in ethyl acetate (50 ml.) and washed three times with water. The ethyl acetate layer is dried over magnesium sulfate, filtered and the filtrate evaporated in vacuo to obtain a residue. The residue is dissolved in chloroform and precipitated with hexane three times, each time discarding the supernatent liquid. The 7-(di-2-thienylacetyl)amino-3-acetoxymethyl-3-cephem-4-carboxylic acid is obtained in a solvent-free form by freeze-drying from a solution in benzene.

NMR: (Solvent — CDCl₃) — Consistent with structure; δ= 4.25

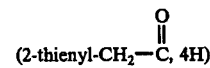

TLC: 1 major spot, $R_f$=0.67 (EtOAC:62, $C_5H_5N$:21, HOAC:6, H₂O:11) on silica gel.

EXAMPLE 23

7-(2-Thienylacetyl)amino-3-acetoxymethyl-3-cephem-4-carboxylic Acid 7-(Phenylacetyl-2-thienylacetyl)amino-3-acetoxymethyl-3-cephem-4-carboxylic acid (250 mg.) is dissolved in tetrahydrofuran (10 ml.) and water (10 ml.). The pH of the solution is adjusted to 9 and the mixture is allowed to stand for one hour. After this the solution is extracted with ethyl acetate and the extracts are washed with a disodium hydrogen phosphate solution. After drying the solvent is evaporated to afford a mixture of the 7-(2-thienylacetyl)amino-3-acetoxymethyl-3-cephem-4-carboxylic acid and the starting material. The product is separated from the starting material by chromatography to afford substantially pure 7-(2-thienylacetyl)amino-3-acetoxymethyl-3-cephem-4-carboxylic acid. The ratio of these two products is 7:3.

The cephalosporins produced by the process of this invention are valuable antibiotics active against various gram-positive and gram-negative bacteria. Thus, 3-acetoxymethyl-7β-(2-thienylacetamido)-3-cephem-4-carboxylic acid, also known generically as cephalothin, is a valuable antibiotic used as a human therapeutic agent. The 7-methoxy cephalosporins have biological spectrums similar to unsubstituted cephalosporins and, in addition, possess other distinctive properties. Thus, in general, they are active against many microorganisms which are resistant to the known cephalosporins such as cephaloridine and cephalothin and are resistant to the β-lactamase produced by cephalosporin resistant clinical isolates of pathogens such as *E. coli* and *A. cloacae.* Also, they are generally more active against strains of Proteus such as mirabilis, and are active against strains of *Proteus morganii* which are resistant to the unsubstituted cephalosporins. They are useful in separating microorganisms in remaining susceptible microorganisms from pharmaceutical, medical and dental equipment and as bactericides in industrial applications, for example in water-based paints and in the white water of paper mills to inhibit the growth of harmful bacteria.

Thus, the 7-methoxy cephalosporins produced in accordance with the processes of this invention are generally more active than the 7-(D-5'-amino-5'-carboxyvaleramido)-7-methoxycephalosporins against various gram-negative organisms and possess increased activity against gram-positive organisms. For example, these 7-methoxy cephalosporins are active against gram-positive pathogens such as *Staphylococcus aureus* at Minimum Inhibitory Concentrations (MIC) as low as about 1.5 mcg./ml., *Streptococcus pyogenes* at MIC of about 0.7 mcg./ml., and *Diplococcus pneumoniae* at MIC of about 0.7 mcg./ml.; and against gram-negative organisms such as *Aerobacter aerogenes* at MIC of about 3 mcg./ml. *Proteus vulgaris* at MIC of about 1.5 mcg./ml. and *Proteus morganii* at about 6 mcg./ml. Thus, activities of specific products of the foregoing examples that might be mentioned are: 3-carbamoyloxymethyl-7-methoxy-7-phenylacetamido-3-cephem-4-carboxylic acid, *S. pyogenes* MIC 1.56 mcg./ml. and *P. vulgaris* MIC 1.56 mcg./ml.; 3-carbamoyloxymethyl-7-methoxy-7-(2-thienylacetamido)-3-cephem-4-carboxylic acid, *S. pyogenes* MIC 0.78 mcg./ml. and *P. morganii* MIC 12.5 mcg./ml; 3 carbamoyloxymethyl-7-methoxy-7-(2-furylacetamido)-3-cephem-4-carboxylic acid, *S. aureus* MIC 6.25 mcg./ml. and *P. vulgaris* MIC 1.56 mcg./ml.; 3-carbamoyloxymethyl-7-methoxy-7-thiophenoxyacetamido-3-cephem-4-carboxylic acid, *S. pyogenes* MIC 0.78 mcg./ml. and *D. pneumoniae* MIC 0.78 mcg./ml.; 3-acetoxymethyl-7-methoxy-7-(2-thienylacetamido)-3-cephem-4-carboxylic acid, *S. pyogenes* MIC 1.56 mcg./ml. and *P. vulgaris* MIC 0.78 mcg./ml.; and 3-pyridiniummethyl-7-methoxy-7-(2-thienylacetamido)-3-cephem-4-carboxylic acid Serratia MIC 25 mcg./ml. and *S. aureus* MIC 156 mcg./ml.

The products of this invention may be used alone or in combination as the active ingredient in any one of a variety of pharmaceutical preparations. These antibiotics and their corresponding salts may be employed in capsule form or as tablets, powders or liquid solutions or as suspensions or elixirs. They may be administered orally, intravenously or intramuscularly. Suitable carriers which may be used in the composition include, for example, mannitol, sucrose, glucose or sterile liquids such as water, saline, glycols and oils of a petroleum, animal, vegetable or synthetic origin as, for example, peanut oil, mineral oil, or sesame oil. Also, in addition to a carrier, the instant compositions may include other ingredients such as stabilizers, binders, antioxidants, preservatives, lubricators, suspending agents, viscosity agents or flavoring agents and the like. In addition, there may also be included in the composition other active ingredients including other antibiotics to provide a broader spectrum of antibiotic activity.

EXAMPLE 24

To a solution of 19.6 g. of ethyl urethane and 27.8 ml. of triethylamine in 300 ml. of benzene cooled to 15° C. is added dropwise 12.1 ml. of dimethyldichlorosilane while maintaining the temperature below about 18° C. The resulting reaction mixture is allowed to stir for 15 minutes, filtered and the cake washed with a small amount of benzene. The filtrate and washes are concentrated to about 30 ml. in vacuo and then filtered and the cake washed with a small amount of benzene. The resulting filtrate and washes are placed under reduced pressure overnight, whereupon the bis-(ethoxycarbonylamino)dimethyl silane of the formula

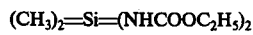

$(CH_3)_2=Si=(NHCOOC_2H_5)_2$ crystallizes out and is separated and dried in vacuo.

A mixture of 100 mg. of di(methoxymethyl) 3-carbamoyloxymethyl-7-methoxy-7β-(D-5-trichloroethoxycarbonylamino-5'-carboxyvaleramido)-3-cephem-4-carboxylate, 135 μl. of α-pinene, 164 mg. of the dimethylsilane described above, 70 μl. of thienylacetyl chloride, and 2.4 ml. of dichloroethane are heated together at 65° C. for 1 hour. Chromatography of the resulting product showed that the desired imide, di(methoxymethyl) 3-carbamoyloxymethyl-7-methoxy-7β-[(D-5'-trichloroethoxycarbonylamino-5'-carboxyvaleryl)-thienylacetylamino]-3-cephem-4-carboxylate, is produced.

EXAMPLE 25

To 1 g. of di(methoxymethyl) 7β-(D-5-trichloroethoxycarbonylamino-5-carboxyvaleramido)-3-carbamoyloxymethyl-7-methoxy-3-cephem-4-carboxylate dissolved in 24 ml. dichloroethane containing 1.35 ml. α-pinene is added 1.7 g. of N-trimethylsilyldiphenyl phosphonamide which is conveniently prepared from diphenyl phosphochloridate and hexamethyl disilazane.

To this mixture is added 0.7 ml. thienylacetyl chloride and the temperature is raised to 65° C. and maintained there for 12 hours. After the mixture is cooled to room temperature it is added to a solution of 50 ml. of 2% NaCl-2.5% NaHCO₃ and 3 ml. of methanol is added. The two layers are vigorously stirred for 15 minutes at room temperature.

The layers are separated and the organic layer added to ice cold hexane (250 ml.). The gum, after decantation of the hexane, is re-dissolved in methylene chloride and the hexane precipitation repeated. Di(methoxymethyl) 7β-[(D-5-trichloroethoxycarbonylamino-5-carboxyvaleryl)-thienylacetylamino-3-carbamoyloxymethyl]-7-methoxy-3-cephem-4-carboxylate so obtained is ready for further processing.

EXAMPLE 26

To 1 g. of imide methoxymethyl ester (obtained as described in Example 25) dissolved in dichloroethane (10 ml.) containing 2 ml. of α-pinene is added 0.3 ml. of trimethylsilyl chloride. The solution is heated at 65° C. for 1½ hours under a nitrogen atmosphere. The solvent is removed in vacuo and the residue is dissolved in 5 ml. of ethyl acetate. To this is added 5 ml. of benzene and the solution is cooled to 0° C. for several hours. The methoxymethyl ester of 3-carbamoyloxymethyl-7-methoxy-7β-(2-thienylacetamido)-3-cephem-4-carboxylic acid is filtered off, washed with 5 ml. cold benzene/ethyl acetate (1:1) and dried in vacuo.

EXAMPLE 27

Two grams of di(methoxymethyl) 7β-(D-5-trichloroethoxycarbonylamino-5-carboxyvaleramido)-3-carbamoyloxymethyl-7-methoxy-3-cephem-4-carboxylate dissolved in 48 ml. of dichloroethane containing 2 ml. of α-pinene is treated with 1.9 g. of N-trimethylsilyl methane sulfonamide followed by 1.4 ml. of thienylacetyl chloride. The clear solution is heated at 65° C. for 12 hours under nitrogen atmosphere. After the solution is cooled to room temperature, it is added dropwise to 500 ml. ice cold hexane. The hexane is decanted from the gum and discarded. The gum is re-dissolved in 20 ml. of methylene chloride and re-precipitated using 500 ml. of cold hexane. The gum, after decantation of the hexane, is dissolved in a mixture of 75 ml. ethyl acetate and 25 ml. methanol. The solution is cooled to 0° C., 2 ml. of concentrated HCl is added and the mixture kept at 0° C. for 90 minutes. The solution is added to 52 ml. water containing 5.2 g. NaHCO$_3$. The bicarbonate layer is extracted with 2 × 20 ml. ethyl acetate and the ethyl acetate layer is discarded. The pH of the bicarbonate layer is adjusted to 1.8 and extracted with 3 × 25 ml. ethyl acetate. On concentration of the organic layer in vacuo, 3-carbamoyloxymethyl-7-methoxy-7β-(2-thienylacetamido)-3-cephem-4-carboxylic acid crystallizes out.

The cephalosporins produced by the process of this invention are valuable antibiotics active against various gram-positive bacteria. Thus, 3-acetoxymethyl-7β-(2-thienylacetamido)-3-cephem-4-carboxylic acid, also known generically as cephalothin, is a valuable antibiotic used as a human therapeutic agent. The 7-methoxy cephalosporins have biological spectrums similar to unsubstituted cephalosporins and, in addition, possess other distinctive properties. Thus, in general, they are active against many microorganisms which are resistant to the known cephalosporins such as cephaloridine and cephalothin and are resistant to the β-lactamase produced by cephalosprin resistant clinical isolates of pathogens such as *E. coli* and *A. cloacae*. Also, they are generally more active against strains of Proteus such as mirabilis, and are active against strains of *Proteus morganii* which are resistant to the unsubstituted cephalosprins. They are useful in separating microorganisms in remaining susceptible microorganisms from pharmaceutical, medical and dental equipment and as bactericides in industrial applications, for example in water-based paints and in the white water of paper mills to inhibit the growth of harmful bacteria.

Thus, the 7-methoxy cephalosporins produced in accordance with the processes of this invention are generally more active than the 7-(D-5'-amino-5'-carboxyvaleramido)-7-methoxycephalosporins against various gram-negative organisms and possess increased activity against gram-positive organisms. For example, these 7-methoxy cephalosporins are active against gram-positive pathogens such as *Staphylococcus aureus* at Minimum Inhibitory Concentrations (MIC) as low as about 1.5 mcg./ml., *Streptococcus pyogenes* at MIC of about 0.7 mcg./ml., and *Diplococcus pneumoniae* at MIC of about 0.7 mcg./ml.; and against gram-negative organisms such as *Aerobacter aerogenes* at MIC of about 3 mcg./ml. *Proteus vulgaris* at MIC of about 1.5 mcg./ml. and *Proteus morganii* at about 6 mcg./ml. Thus, activities of specific products of the foregoing examples that might be mentioned are: 3-carbamoyloxymethyl-7-methoxy-7-phenylacetamido-3-cephem-4-carboxylic acid, *S. pyogenes* MIC 1.56 mcg./ml. and *P. vulgaris* MIC 1.56 mcg./ml.; 3-carbamoyloxymethyl-7-methoxy-7-(2-thienylacetamido)-3-cephem-4-carboxylic acid, *S. pyogenes* MIC 0.78 mcg./ml. and *P. morganii* MIC 12.5 mcg./ml; 3-carbamoyloxymethyl-7-methoxy-7-(2-furylacetamido)-3-cephem-4-carboxylic acid, *S. aureus* MIC 6.25 mcg./ml. and *P. vulgaris* MIC 1.56 mcg./ml.; 3-carbamoyloxymethyl-7-methoxy-7-thiophenoxyacetamido-3-cephem-4-carboxylic acid, *S. pyogenes* MIC 0.78 mcg./ml. and *D. pneumoniae* MIC 0.78 mcg./ml.; 3-acetoxymethyl-7-methoxy-7-(2-thienylacetamido)-3-cephem-4-carboxylic acid, *S. pyogenes* MIC 1.56 mcg./ml. and *P. vulgaris* MIC 0.78 mcg./ml.; and 3-pyridiniummethyl-7-methoxy-7-(2-thienylacetamido)-3-cephem-4-carboxylic acid *Serratia* MIC 25 mcg./ml. and *S. aureus* MIC 156 mcg./ml.

The products of this invention may be used alone or in combination as the active ingredient in any one of a variety of pharmaceutical preparations. These antibiotics and their corresponding salts may be employed in capsule form or as tablets, powders or liquid solutions or as suspensions or elixirs. They may be administered orally, intravenously or intramuscularly. Suitable carriers which may be used in the composition include, for example, mannitol, sucrose, glucose or sterile liquids such as water, saline, glycols and oils of a petroleum, animal, vegetable or synthetic origin as, for example, peanut oil, mineral oil, or sesame oil, Also, in addition to a carrier, the instant compositions may include other ingredients such as stabilizers, binders, antioxidants, preservatives, lubricators, suspending agents, viscosity agents or flavoring agents and the like. In addition, there may also be included in the composition other active ingredients including other antibiotics to provide a broader spectrum of antibiotic activity.

Although the salts of cephalosporins are generally used as therapeutic agents, certain esters of these cephalosporins are also expecially useful for human and animal therapy. Especially preferred are those esters which are converted biologically to the free acid or a salt thereof. Examples of such esters that might be mentioned are loweralkyloxy loweralkyl esters such as methoxymethyl, methoxyethyl, and the like; aralkyloxy loweralkyl esters such as benzyloxymethyl, benzyloxyethyl, and the like; aryloxy loweralkyl esters such as phenoxymethyl, phenoxyethyl, and the like; and acyloxy loweralkyl esters such as the acetoxymethyl, pivaloyloxymethyl, pivaloyloxyethyl, propionyloxymethyl, butyryloxymethyl, isobutyryloxymethyl, benzoyloxymethyl ester and the like. The term "loweralkyl" refers to straight or branched chain alkyl groups having 1 to 5 carbon atoms. These esters can be prepared directly by using the desired ester in the above-described processes and recovering the ester of the desired cephalosporin compound. For example, when the methoxymethyl ester of the 7β-adipoyl cephalosporin compound is used in the above-described transacylation process, the methoxymethyl ester of the new 7β-acylamidocephalosporin compound is produced directly as is shown in the foregoing examples. Alternatively, the cephalosporin free acids produced by the processes of this invention are readily esterified by reaction with the appropriate haloloweralkyl moiety in accordance with methods well known in the art. Thus, for example, the methoxymethyl ester and the phenoxymethyl ester are readily prepared by reacting chloromethyl methyl ether or α-chloroanisole with the cephalosporin acid in the presence of an acid scavenger, or by reacting a salt of the cephalosporin acid with the halo compound. Similarly, the acyloxyloweralkyl esters are readily prepared by reacting the cephalosporin acid or a salt thereof with the chloro or bromomethyl ester of the appropriate acid pursuant to methods known in the art.

We claim:
1. A cephalosporin compound of the formula:

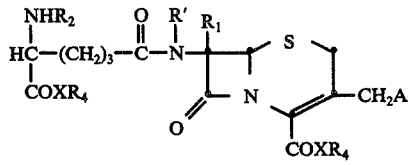

wherein $R_2$ is hydrogen, trichloroethoxycarbonyl, t-butoxycarbonyl, trimethylsilyl, p-methoxybenzyloxy, 2-nitrophenyl-sulfenyl, 2,4-dinitrophenylsulfenyl, chloroacetyl, or o-nitrophenylthio;

X is oxygen or sulfur;

$R_4$ is hydrogen, methyl, ethyl, t-butyl, phthalimidomethyl, succinimidomethyl, phenacyl, p-bromophenacyl, 2,2,2-trichloroethyl, 2-methylthioethyl, 2-(p-methylphenyl)ethyl, methoxymethyl, 2-(p-methylphenyl)sulfonylethyl, 2-methylaminoethyl, benzyloxymethyl, p-methoxybenzyl, 3,5-dinitrobenzyl, 2-chloroethyl, 2-bromoethyl, benzyl, p-nitrobenzyl, 2,4,6-trimethylbenzyl, 3,5-dichloro-4-hydroxybenzyl, benzhydryl, p-methoxybenzhydryl, acetoxymethyl, pivaloyloxymethyl, methoxymethyl, phenyl, p-nitrophenyl, or 3,5-dinitrophenyl;

$R_1$ is hydrogen or methoxy;

R' is phenylacetyl, thienylacetyl, furylacetyl, phenoxyacetyl, phenylthioacetyl, α-azidophenylacetyl or trifluoroacetyl; and A is carbamoyloxy.

2. The compound of claim 1 wherein $R_2$ is trichloroethylcarbonyl, chloroacetyl, t-butoxycarbonyl, 2-nitrophenylsulfenyl, or 2,4-dinitrophenylsulfenyl;

X is oxygen; and $R_4$ is methoxymethyl, benzhydryl, or benzyloxymethyl.

3. The product of claim 2 wherein R' represents 2-thienylacetamido.

4. The product of claim 3 wherein $R_1$ represents hydrogen.

5. The product of claim 3 wherein $R_1$ represents methoxy.

* * * * *